(12) United States Patent
Ebright et al.

(10) Patent No.: US 9,221,880 B2
(45) Date of Patent: *Dec. 29, 2015

(54) ANTIBACTERIAL AGENTS: SALINAMIDE DERIVATIVES

(71) Applicant: Rutgers, The State University of New Jersey, New Brunswick, NJ (US)

(72) Inventors: Richard H. Ebright, New Brunswick, NJ (US); Yon W. Ebright, New Brunswick, NJ (US); Yu Feng, New Brunswick, NJ (US); David Degen, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,914

(22) Filed: Dec. 12, 2013

(65) Prior Publication Data

US 2014/0162939 A1    Jun. 12, 2014

Related U.S. Application Data

(60) Provisional application No. 61/736,476, filed on Dec. 12, 2012.

(51) Int. Cl.
| | | |
|---|---|---|
| C07K 11/02 | (2006.01) | |
| A61K 38/12 | (2006.01) | |
| A61P 31/04 | (2006.01) | |

(52) U.S. Cl.
CPC ..................... *C07K 11/02* (2013.01)

(58) Field of Classification Search
CPC ...................................................... C07K 11/02
See application file for complete search history.

(56) References Cited

U.S. PATENT DOCUMENTS

| | | | |
|---|---|---|---|
| 5,688,783 A | * | 11/1997 | Fenical et al. ............. 514/183 |
| 5,919,926 A | | 7/1999 | Fenical et al. |
| 2014/0162940 A1 | | 6/2014 | Ebright et al. |

OTHER PUBLICATIONS

Anstee et al., "Inhibition of bacterial RNA polymerases: peptide metabolites from the cultures of Streptomyces sp", *J. Nat. Prod.* 60, 858-861 (1997).

Chopra, "Bacterial RNA polymerase: a promising target for the discovery of new antimicrobial agents", *Curr. Opin. Investig. Drugs* 8, 600-607 (2007).
Darst, "New inhibitors targeting bacterial RNA polymerase", *Trends Biochem. Sci.* 29 (4), 159-162 (2004).
Ho et al., "Structures of RNA polymerase-antibiotic complexes". *Curr. Opin. Struct. Biol.* 19, 715-723 (2009).
Srivastava et al., :New Target for Inhibition of Bacterial RNA Polymerase: "Switch Region", *Curr. Opin. Microbiol.* 14, 532-543 (2011).
Trischman et al., "Salinamides A and B: anti-inflammatory depsipeptides frm a marine streptomycete", *J. Am. Chem. Soc.* 116, 757-758 (1994).
Trischman et al., "Salinamides: anti-inflammatory depsipeptides from a marine streptomycete", *J. Org. Chem.* 64, 1145-1150 (1999).
Villain-Guillot et al., "Progress in targeting bacterial transcription", *Drug Discov. Today* 12 (5/6), 200-208 (2007).

* cited by examiner

*Primary Examiner* — Julie Ha
*Assistant Examiner* — Li Ni Komatsu
(74) *Attorney, Agent, or Firm* — Viksnins Harris & Padys PLLP

(57) ABSTRACT

The invention provides compounds of formula (I):

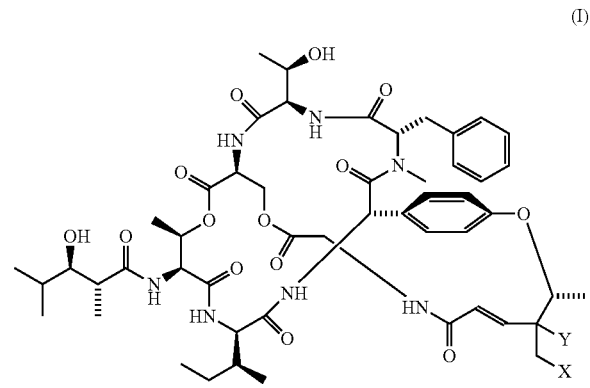

and salts thereof, wherein X and Y have any of the values defined herein. The compounds inhibit bacterial RNA polymerase, inhibit bacterial growth, and have applications in, analysis of RNA polymerase structure and function, control of bacterial gene expression, control of bacterial growth, antibacterial chemistry, antibacterial therapy, and drug discovery.

15 Claims, 4 Drawing Sheets

A

| dataset | Eco RNAP | Eco RNAP-Sal |
|---|---|---|
| space group | P2 (1) 2 (1) 2 (1) | P2 (1) 2 (1) 2 (1) |
| resolution range | 50.00-3.90 Å (3.97-3.90 Å) | 50.00-3.90 Å (3.97-3.90 Å) |
| completeness | 0.997 (0.996) | 0.998 (0.997) |
| mean I/σ | 13.2 (1.8) | 15.5 (1.5) |
| Rmerge | 0.115 (0.625) | 0.118 (0.891) |
| Rwork | 0.276 | 0.286 |
| Rfree | 0.325 | 0.325 |
| PDB code | 4MEY | 4MEX |

B

C

ANTIBACTERIAL AGENTS: SALINAMIDE DERIVATIVES

PRIORITY OF INVENTION

This application claims priority from U.S. Provisional Application No. 61/736,476, filed 12 Dec. 2012; the entire content of this provisional application is hereby incorporated herein by reference.

STATEMENT OF GOVERNMENT SUPPORT

The invention described herein was made with United States Government support under Grant Numbers AI072766, AI104660, and GM041376, awarded by the National Institutes of Health. The United States Government has certain rights in the invention.

BACKGROUND

Bacterial infectious diseases kill 100,000 persons each year in the US and 11 million persons each year worldwide, representing nearly a fifth of deaths each year worldwide (Heron et al., Final Data for 2006. National Vital Statistics Reports, Vol. 57 (Centers for Disease Control and Prevention, Atlanta Ga.) and World Health Organization (2008) The Global Burden of Disease: 2004 Update (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. Public Health Reports, 122, 160-166; Scott, R. (2009) The direct medical costs of healthcare-associated infections in U.S. hospitals and benefits of prevention (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a target for antibacterial therapy (Darst, S. (2004) Trends Biochem. Sci. 29, 159-162; Chopra, I. (2007) Curr. Opin. Investig. Drugs 8, 600-607; Villain-Guillot, P., Bastide, L., Gualtieri, M. & Leonetti, J. (2007) Drug Discov. Today 12, 200-208; Ho, M., Hudson, B., Das, K., Arnold, E., Ebright, R. (2009) Curr. Opin. Struct. Biol. 19, 715-723; and Srivastava et al. (2011) Curr. Opin. Microbiol. 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are not highly conserved in human RNAP I, RNAP II, and RNAP III (permitting therapeutic selectivity).

Accordingly, new antibacterial agents are needed.

SUMMARY OF CERTAIN EMBODIMENTS OF THE INVENTION

The invention provides new compositions of matter that inhibit bacterial RNA polymerase and inhibit bacterial growth. The compounds described herein are anticipated to have applications in analysis of RNA polymerase structure and function, control of bacterial gene expression, control of bacterial growth, antibacterial chemistry, antibacterial therapy, and drug discovery.

Accordingly, the invention provides a compound according to general structural formula (I):

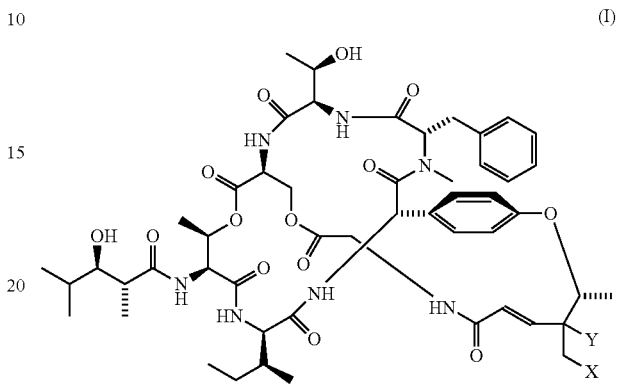

(I)

wherein:

X is one of —Br, —I, —OR, —SR, and —NHR; Y is one of —Br, —I, —OR, —SR, and —NHR; and at least one of X and Y is OH;

each R is independently H or a branched or unbranched, saturated or unsaturated, hydrocarbon chain, having from 3 to 15 carbon atoms, wherein one or more of the carbon atoms is optionally replaced by (—O—) or (—NR$^a$—), and wherein the chain is optionally substituted on carbon with one or more substituents independently selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, heteroaryloxy, a hydrogen-bonding group, and a negatively charged functional group; and each $R^a$ is independently H or ($C_1$-$C_6$)alkyl;

or a salt thereof.

The invention provides methods of structure-based design, synthesis, and assay of a compound according to general structural formula (I).

The invention provides use of a compound according to general structural formula (I), e.g., to promote an antibacterial effect.

The invention also encompasses a crystal structure of a bacterial RNA polymerase in complex with salinamide A and a crystal structure of a bacterial RNA polymerase in complex with a compound according to general structural formula (I).

The compounds of this invention have utility as RNAP inhibitors.

The compounds of this invention have utility as antibacterial agents.

The invention provides novel derivatives of salinamide A that contain replacements of the salinamide A epoxide that, it is believed, provide one or more of the following advantages as compared to the salinamide A epoxide: (1) improvement of interactions with the salinamide binding site and an adjacent pocket on a bacterial RNA polymerase (e.g., improving interactions with a residue corresponding to, and alignable with, one of residues beta678, beta1105, beta1106, beta'731, and beta'736 of Escherichia coli RNA polymerase), (2) increased potency of inhibition of a bacterial RNA polymerase, (3) increased potency of antibacterial activity, (4) increased stability, and (5) decreased genotoxicity.

DETAILED DESCRIPTION OF THE INVENTION

Figure 1:
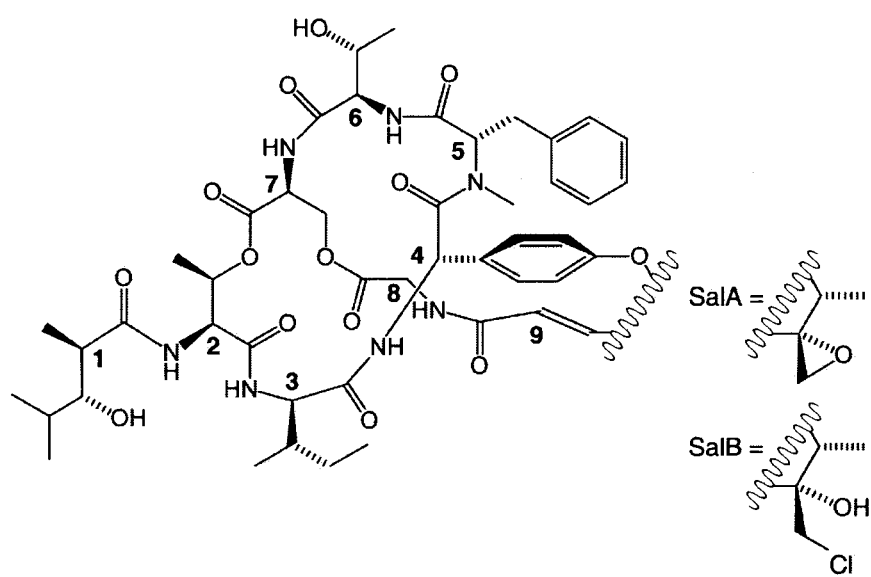
FIG. 1. Structures of SalA (compound 1) and SalB (compound 2).

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, 0, ($C_1$-$C_4$)alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X). The following definitions are used, unless otherwise indicated.

The term "hydrogen-bonding group" includes moieties that contain an O, N, or S atom able to donate or accept a hydrogen bond in aqueous solution, such as, for example, amine, hydroxyl, thiol, ether, thioether, carbonyl, thionyl, carboxyl, thiocarboxyl, amide, thioamide, ester, thioester, sulfonic acid, sulfonic acid ester, sulfonamide, phosphoric acid, phosphoric acid ester, phosphonamide, boronic acid, boronic acid ester, pyrrole, pyrrolidine, carbazole, pyrroline, indole, isoindole, indoline, indolizine, furan, pyran, benzofuran, thiophene, benzothiophene, pyridine, quinoline, isoquinoline, quinazoline, napthyridine, oxazole, isoxazole, benzoxazole, thiazole, isothiazole, benthiazole, oxadiazole, thiadiazole, imidazole, triazole, tetrazole, benzimidazole, pyrazole, pyrazine, pyridazine, pyrimidine, triazine, indazole, purine, pteridine, phthalazine, quinoxaline, quinazoline, cinnoline, acridine, phenazine, phenothiazine, phenoxazine, and ionized forms and salts thereof, as known to those skilled in the art.

The term "negatively charged functional group" includes moieties that contain an O, N, or S atom that predominantly carries a –1 negative charge in aqueous solution at a physiologically relevant pH, between about pH 4 and about pH 10, such as, for example, carboxyl, thiocarboxyl, sulfonic acid, phosphoric acid, phosphoric acid ester, boronic acid, triazole, tetrazole, purine, thiol, and ionized forms and salts thereof, as known to those skilled in the art.

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present compounds are within the scope of the invention. Similarly, E- and Z-isomers, or mixtures thereof, of olefins within the structures also are within the scope of the invention.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Unless otherwise stated, structures depicted herein also are meant to include compounds that differ only by the presence of one or more isotopically enriched atoms. For example, compounds having the present structures except for the replacement of a hydrogen atom by a deuterium or tritium, or the replacement of a carbon by a $^{13}C$- or $^{14}C$-enriched carbon, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. Accordingly, certain embodiments of the invention are directed to salts of the compounds described herein, e.g., pharmaceutically acceptable salts.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

Specific values listed below for radicals, substituents, and ranges, are for illustration only; they do not exclude other defined values or other values within defined ranges for the radicals and substituents Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl can be cyclopropyl, cyclobutyl, cyclopentyl, or cyclohexyl; ($C_1$-$C_6$) alkoxy can be methoxy, ethoxy, propoxy, isopropoxy, butoxy, iso-butoxy, sec-butoxy, pentoxy, 3-pentoxy, or hexyloxy; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Certain embodiments of the present invention provide a compound of general structural formula (I):

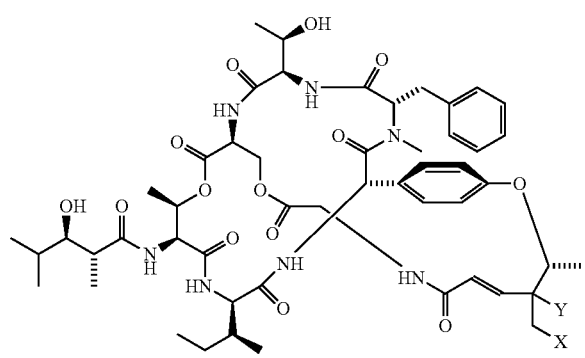

(I)

wherein:
X is one of —Br, —I, —OR, —SR, and —NHR; Y is one of —Br, —I, —OR, —SR, and —NHR; and at least one of X and Y is OH;

R is H or a branched or unbranched, saturated or unsaturated, hydrocarbon chain, having from 3 to 15 carbon atoms, wherein one or more of the carbon atoms is optionally replaced by (—O—) or (—$NR^a$—), and wherein the chain is optionally substituted on carbon with one or more substituents independently selected from the group consisting of ($C_1$-$C_6$)alkoxy, ($C_3$-$C_6$)cycloalkyl, ($C_1$-$C_6$)alkanoyl, ($C_1$-$C_6$) alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, heteroaryloxy, a hydrogen-bonding group, and a negatively charged functional group; and each $R^a$ is independently H or ($C_1$-$C_6$)alkyl;
or a salt thereof.

In certain embodiments the compound of formula (I) is a compound of formula (Ia):

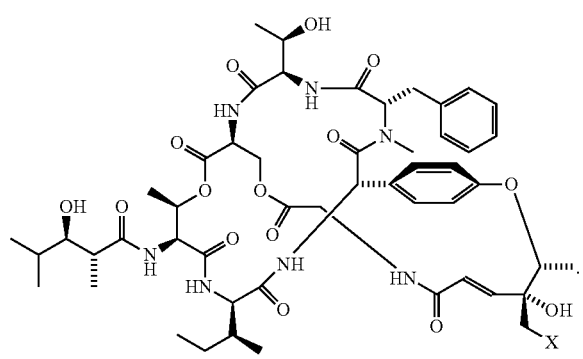

(Ia)

In certain embodiments R is a branched or unbranched, saturated or unsaturated, hydrocarbon chain, having from 3 to 8 carbon atoms, wherein one or more of the carbon atoms is optionally replaced by (—O—) or (—$NR^a$—), and wherein the chain is optionally substituted on carbon with one or more substituents independently selected from the group consisting of ($C_1$-$C_6$)alkoxy, ($C_1$-$C_6$)alkanoyl, ($C_1$-$C_6$)alkanoyloxy, ($C_1$-$C_6$)alkoxycarbonyl, halo, hydroxy, oxo, carboxy, aryl, aryloxy, a hydrogen-bonding group, and a negatively charged functional group.

In certain embodiments, R consists of a chain of about 3 to about 6 consecutively bonded non-hydrogen atoms and preferably contains a hydrogen bonding or negatively charged functional group.

In certain embodiments, X is one of —Br and —I.

In certain embodiments, X is one of —OR, —SR, and —NHR, and R is H or consists of a chain of about 3 to about 8 consecutively bonded non-hydrogen atoms and optionally contains one or more (e.g., 1, 2, or 3) hydrogen-bonding or negatively charged functional groups.

In certain embodiments, X is one of —OR, —SR, and —NHR, and R is H or consists of a chain of about 3 to about 8 consecutively bonded non-hydrogen atoms and contains one or more (e.g., 1, 2, or 3) hydrogen-bonding or negatively charged functional groups.

In certain embodiments, X is one of —OR, —SR, and —NHR, and R is H or consists of a chain of about 3 to about 6 consecutively bonded non-hydrogen atoms and optionally contains one or more (e.g., 1, 2, or 3) hydrogen-bonding or negatively charged functional groups.

In certain embodiments, X is one of —OR, —SR, and —NHR, and R is H or consists of a chain of about 3 to about 6 consecutively bonded non-hydrogen atoms and contains one or more (e.g., 1, 2, or 3) hydrogen-bonding or negatively charged functional groups.

In certain embodiments, X is one of —O($CH_2$)$_n$C(OH)(R')R", —O($CH_2$)$_n$C(O)R', —O($CH_2$)$_n$C(O)OR', —O($CH_2$)$_n$C(O)NR'R", —O($CH_2$)$_n$OC(H)(R')R", —S($CH_2$)$_n$C(OH)(R')R", —S($CH_2$)$_n$C(O)R', —S($CH_2$)$_n$C(O)OR', —S($CH_2$)$_n$C(O)NR'R", —S($CH_2$)$_n$OC(H)(R')R", —NH($CH_2$)$_n$C(OH)(R')R", —NH($CH_2$)$_n$C(O)R', —NH($CH_2$)$_n$C(O)OR', —NH($CH_2$)$_n$C(O)NR'R", and —NH($CH_2$)$_n$OC(H)(R')R"; wherein n is 1, 2, 3, 4, 5, 6, or 7; and wherein R' and R" each independently is one of H, $C_1$-$C_3$alkyl, and $C_1$-$C_3$ alkyl substituted by one or more (e.g. 1, 2, or 3) halogen.

In certain embodiments, Y is OH.

In certain embodiments, Y is one of —Br and —I.

In certain embodiments, Y is one of —OR, —SR, and —NHR, and R is H or consists of a chain of about 3 to about 8 consecutively bonded non-hydrogen atoms and optionally contains one or more (e.g., 1, 2, or 3) hydrogen-bonding or negatively charged functional groups.

In certain embodiments, Y is one of —OR, —SR, and —NHR, and R is H or consists of a chain of about 3 to about 8 consecutively bonded non-hydrogen atoms and contains one or more (e.g., 1, 2, or 3) hydrogen-bonding or negatively charged functional groups.

In certain embodiments, Y is one of —OR, —SR, and —NHR, and R is H or consists of a chain of about 3 to about 6 consecutively bonded non-hydrogen atoms and optionally contains one or more (e.g., 1, 2, or 3) hydrogen-bonding or negatively charged functional groups.

In certain embodiments, Y is one of —OR, —SR, and —NHR, and R is H or consists of a chain of about 3 to about 6 consecutively bonded non-hydrogen atoms and contains one or more (e.g., 1, 2, or 3) hydrogen-bonding or negatively charged functional groups.

In certain embodiments, Y is one of —O($CH_2$)$_n$C(OH)(R')R", —O($CH_2$)$_n$C(O)R', —O($CH_2$)$_n$C(O)OR', —O($CH_2$)$_n$C(O)NR'R", —O($CH_2$)$_n$OC(H)(R')R", —S($CH_2$)$_n$C(OH)(R')R", —S($CH_2$)$_n$C(O)R', —S($CH_2$)$_n$C(O)OR', —S($CH_2$)$_n$C(O)NR'R", —S($CH_2$)$_n$OC(H)(R')R", —NH($CH_2$)$_n$C(OH)(R)R", —NH($CH_2$)$_n$C(O)R', —NH($CH_2$)$_n$C(O)OR', —NH($CH_2$)$_n$C(O)NR'R", and —NH($CH_2$)$_n$OC(H)(R')R"; wherein n is 1, 2, 3, 4, 5, 6, or 7; and wherein R' and R" each independently is one of H, $C_1$-$C_3$alkyl, and $C_1$-$C_3$ alkyl substituted by one or more (e.g. 1, 2, or 3) halogen.

In certain embodiments, n is 1, 2, 3, 4, or 5.

Certain embodiments of the present invention provide a method of structure-based design of a compound described here that includes inspection of a crystal structure of a bacterial RNA polymerase in complex with one of salinamide A and a compound described herein.

Certain embodiments of the present invention provide a method of synthesis of a compound described herein, comprising reaction of salinamide A with HX in the presence of an acid.

Certain embodiments of the present invention provide a method of synthesis of a compound described herein, comprising reaction of salinamide A with HX in the presence of a base.

Certain embodiments of the present invention provide a method of synthesis of a compound described herein, comprising reaction of salinamide A with YX, wherein Y is a cation.

Certain embodiments of the present invention provide a method of synthesis of a compound described herein, comprising reaction of salinamide B with HX in the presence of a base.

Certain embodiments of the present invention provide a method of synthesis of a compound described herein, comprising reaction of salinamide B with YX, wherein Y is a cation.

Certain embodiments of the present invention provide an assay for inhibition of a RNA polymerase comprising contacting a bacterial RNA polymerase with a compound described herein.

Certain embodiments of the present invention provide an assay for potential antibacterial activity comprising contacting a bacterium with a compound described herein.

Certain embodiments of the present invention provide a use of a compound described herein as an inhibitor of a bacterial RNA polymerase.

Certain embodiments of the present invention provide a use of a compound described herein as an antibacterial agent.

Certain embodiments of the present invention provide a use of a compound described herein as one of a disinfectant, a sterilant, an antispoilant, an antiseptic, and an antiinfective.

Certain embodiments of the present invention provide a pharmaceutical composition comprising a compound of formula (I), or a pharmaceutically acceptable salt thereof, and a pharmaceutically acceptable carrier.

Certain embodiments of the present invention provide a compound of formula (I), or a pharmaceutically acceptable salt thereof, for use in therapy.

Certain embodiments of the present invention provide a method to treat a bacterial infection in an animal (e.g. a mammal, such as a human) comprising administering a compound of formula (I), or a pharmaceutically acceptable salt thereof, to the animal.

The invention also provides a synthetic intermediate of formula 7 or 9:

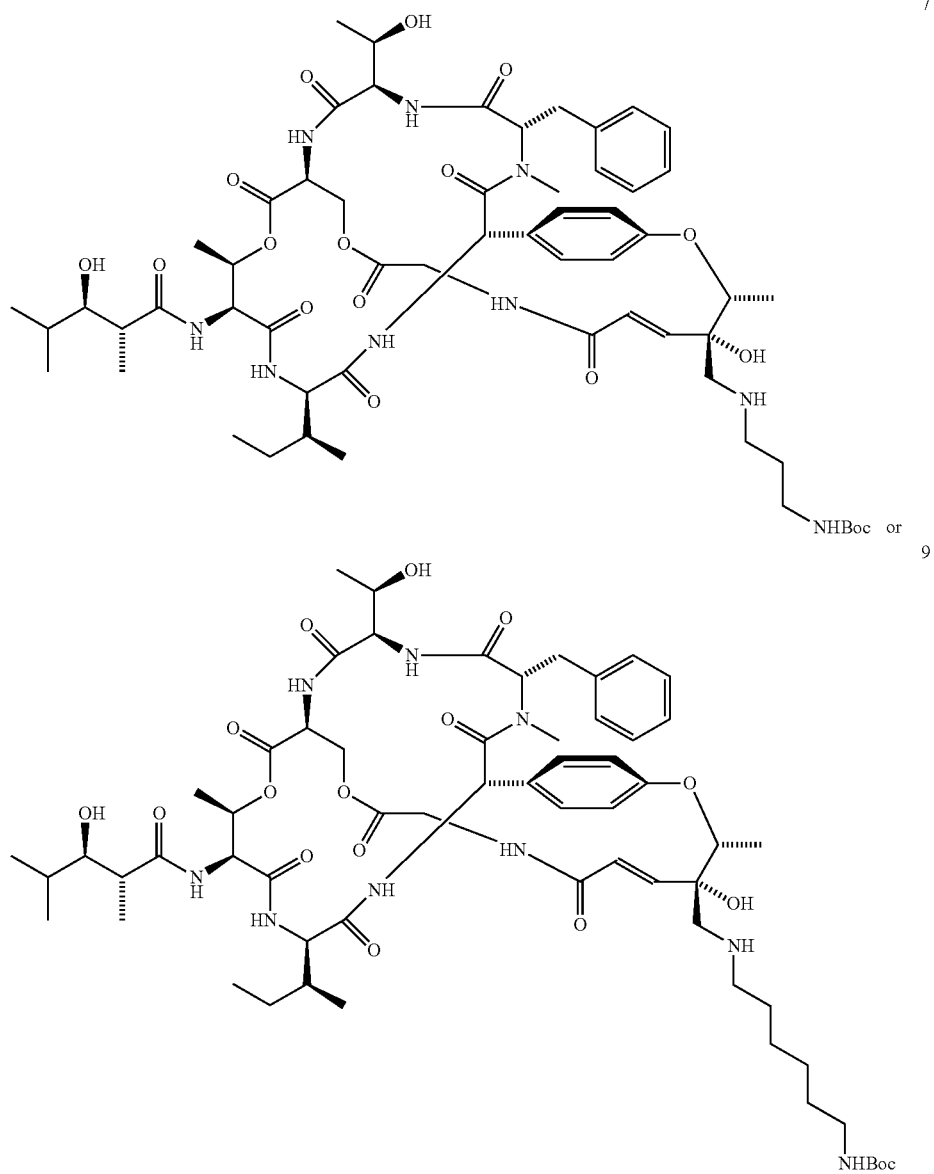

or a salt thereof. The synthetic intermediates are useful for preparing other compounds of formula (I).

Applicant has synthesized the compound according to general structural formula (I) wherein X is bromine.

Applicant has shown that the compound according to general structural formula (I) wherein X is bromine potently inhibits bacterial RNA polymerase (RNAP) in vitro (*Escherichia coli* RNAP; IC50=0.78±0.05 μM [radiochemical assay]; *Staphylococcus aureus* RNAP; IC50=0.54±0.04 μM [radiochemical assay]), and does not detectably inhibit human RNAP I, II, and III (IC50>100 μM [radiochemical assay])

Applicant has shown that the compound according to general structural formula (I) wherein X is bromine exhibits potent antibacterial activity against Gram-negative bacteria in culture (*Escherichia coli* D21f2tolC, MIC50=0.049 μg/ml; *Enterobacter cloacae*, MIC50=1.56 μg/ml; *Neisseria gonorrhoeae*, MIC50=1.56 μg/ml; *Haemophilus influenzae*, MIC50=6.25 μg/ml; *Pseudomonas aeruginosa*, MIC50=50 μg/ml), and does not detectably inhibit growth of mammalian cells in culture (Vero E6 cells, MIC>50 μg/ml).

Applicant has synthesized the compounds according to general structural formula (I) wherein X is —OH, —OBu, —NH(CH$_2$)$_3$NHBoc, and —NH(CH$_2$)$_3$NHBoc).

Applicant has shown that the compounds according to general structural formula (I) wherein X is —OH, —OBu, —NH(CH$_2$)$_3$NHBoc, or —NH(CH$_2$)$_3$NHBoc potently inhibit bacterial RNAP in vitro (*Escherichia coli* RNAP; IC50s=0.3-6 μM [fluorescence-detected assays]; Table 1).

Applicant has shown that the compounds according to general structural formula (I) wherein X is —OH, —OBu, —NH(CH$_2$)$_3$NHBoc, or —NH(CH$_2$)$_3$NHBoc exhibit potent antibacterial activity against Gram-negative bacteria in culture (*Escherichia coli* D21f2tolC, MIC50s=0.78-1.56 μg/ml; *Enterobacter cloacae*, MIC50s=12.5-100 μg/ml; Table 2). Applicant has determined crystal structures of (1) *Escherichia coli* RNAP in complex with salinamide A and (2) *Escherichia coli* RNAP in complex with the compound according to general structural formula (I) wherein X is bromine. The crystal structures enable structure-based design of compounds according to general structural formula (I).

Salinamides

Compounds according to general structural formula (I) are analogs of salinamide A (Sal; SalA; compound 1) and salinamide B (SalB; compound 2).

SalA and SalB are bicyclic depsipeptides, each consisting of seven amino-acid residues and two non-amino-acid residues (Trischman et al., *J. Am. Chem. Soc.*, 116:757-758, 1994; Moore et al., *J. Org. Chem.*, 64:1145-1150, 1999; FIG. 1). Residue 9 of SalA contains an epoxide moiety. Residue 9 of SalB contains a chlorohydrin moiety.

SalA and SalB are produced by *Streptomyces* sp. CNB-091, a marine bacterium isolated from the surface of the jellyfish *Cassiopeia xamachana* (Trischman et al., *J. Am. Chem. Soc.*, 116:757-758, 1994; Moore et al., *J. Org. Chem.*, 64:1145-1150, 1999; Moore & Seng, *Tetrahedron Lett.* 39:3915-3918, 1998). SalA also is produced by *Streptomyces* sp. NRRL 21611, a soil bacterium (Miao et al., *J. Nat. Prod.* 60, 858-861, 1997).

A total synthesis of SalA has been reported (Tan & Ma, *Angew. Chem. Int. Ed.* 47:3614-3617, 2008).

Salinamides: RNAP-Inhibitory Activity and Antibacterial Activity

It has been reported previously that SalA inhibits Gram-positive and Gram-negative bacterial RNAP in vitro (Miao et al., *J. Nat. Prod.* 60, 858-861, 1997). It is disclosed herein that SalB also inhibits Gram-positive and Gram-negative bacterial RNAP in vitro. It further is disclosed herein that SalA and SalB do not detectably inhibit human RNAP I, II, and III.

It has been reported previously that SalA and SalB exhibit antibacterial activity against Gram-positive bacterial pathogens (Trischman et al., *J. Am. Chem. Soc.*, 116:757-758, 1994; Moore et al., *J. Org. Chem.*, 64:1145-1150, 1999). It is disclosed herein that SalA and SalB exhibit antibacterial activity against Gram-negative bacterial pathogens, including *Enterobacter cloacae, Haemophilus influenzae, Neisseria gonorrhoeae*, and *Pseudomonas aeruginosa*. It further is disclosed herein that SalA and SalB do not detectably inhibit growth of mammalian cells in culture.

The inhibition of bacterial RNAP by Sal accounts, in part or in whole, for the antibacterial activity of Sal (Ebright et al., WO/2012/129173, 2012). Sal inhibits RNA synthesis not only in vitro but also in bacterial cells in culture (Ebright et al., WO/2012/129173, 2012). Mutations in genes encoding RNAP beta and beta' subunits confer resistance to the antibacterial activity of Sal (Ebright et al., WO/2012/129173, 2012).

Salinamides: Binding Site on RNAP

The binding site on bacterial RNAP for Sal—the "Sal target" (also referred to as the "bridge-helix-cap target")—was identified by mapping sites of substitutions that confer Sal-resistance onto the three-dimensional structure of RNAP (Ebright et al., WO/2012/129173, 2012).

The binding site on bacterial RNAP for Sal was confirmed by determining crystal structures of *Escherichia coli* RNAP holoenzyme in the absence of Sal (resolution=4.0 Å) and *Escherichia coli* RNAP holoenzyme in the presence of Sal (resolution=4.2 Å) (Ebright et al., WO/2012/129173, 2012). Comparison of electron density maps revealed difference density attributable to Sal. The difference density was located in the Sal target and was in contact with or close to sites of substitutions conferring Sal resistance are obtained. The resolution was sufficient to conclude that the Sal target is the binding site on RNAP for Sal, and that sites of substitutions that confer Sal-resistance correspond to RNAP residues of RNAP that contact or are close to Sal. However, the resolution was insufficient to define the orientation of Sal relative to the Sal target and to define interatomic contacts between Sal and the Sal target.

Figure 2:
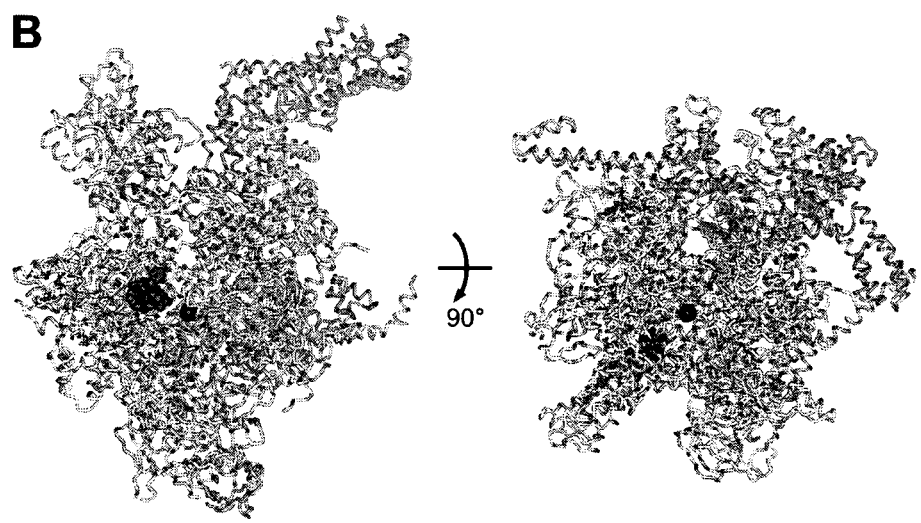
FIG. 2. Crystal structure of RNAP in complex with Sal: overview. (A) Crystallization and refinement statistics for crystal structure of *Escherichia coli* RNAP holoenzyme in complex with SalA at 3.9 Å resolution. (B) Overall structure (two orthogonal views; gray surface labelled "*," SalA; dark sphere, RNAP active-center $Mg^{2+}$ ion). (C) Electron density and model for SalA [two orthogonal views; mesh, $F_o$–$F_c$ omit map for SalA (NCS averaged and contoured at 3.2σ); BH, bridge helix; FL, fork loop; LR, link region.
Figure 2:
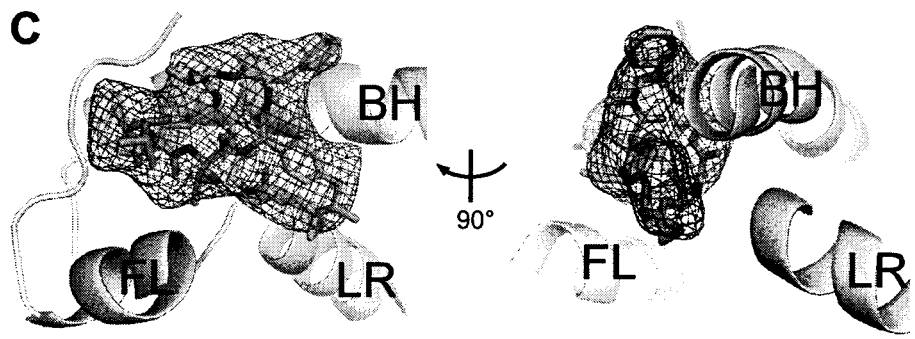
Figure 3:
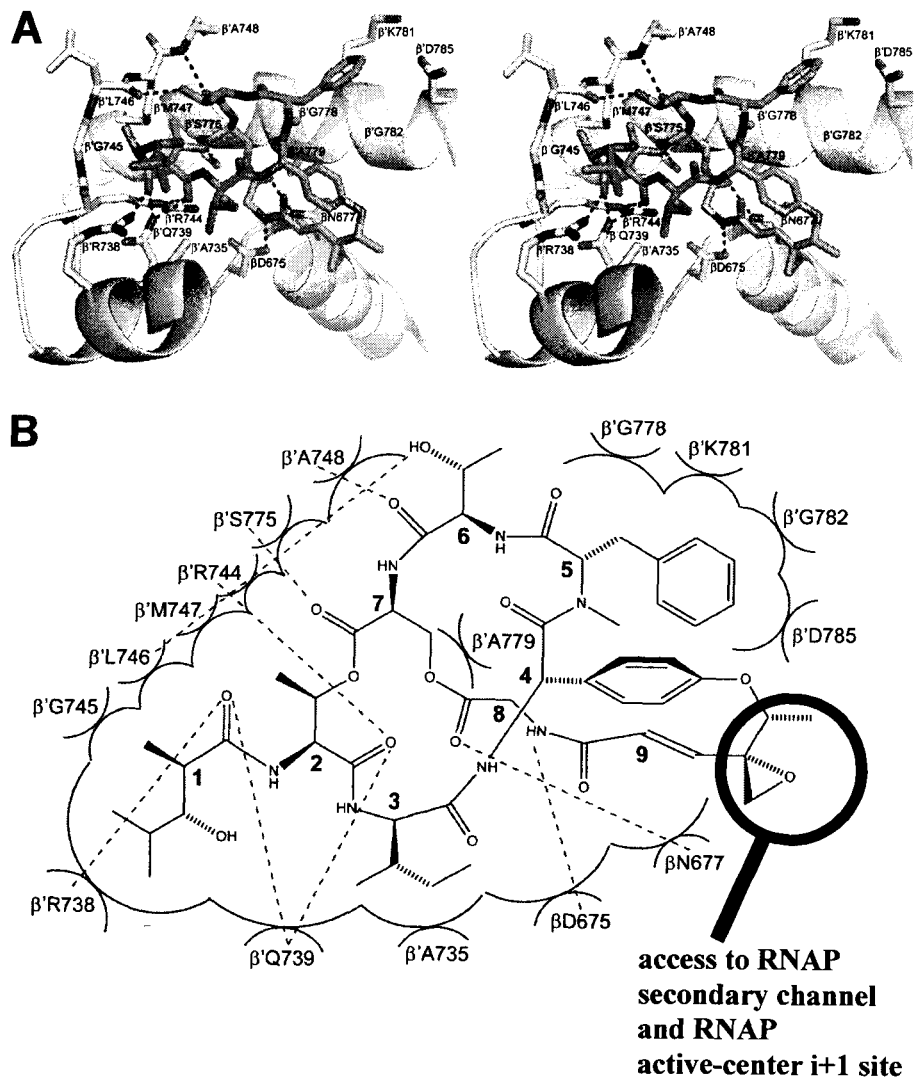
FIG. 3. Crystal structure of RNAP in complex with Sal: details. (A) Stereoview showing RNAP-Sal interactions as observed in the crystal structure of *Escherichia coli* RNAP holoenzyme in complex with SalA at 3.9 Å resolution. Gray, RNAP backbone (ribbon representation) and RNAP sidechain atoms (stick representation). Dashed lines, H-bonds. (B) Schematic summary of contacts between RNAP and SalA. Black circle, part of SalA that has unobstructed access to RNAP secondary channel and RNAP active-center i+1 site. Dashed lines, H-bonds. Arcs, van der Waals interactions.

Disclosed herein are crystal structures of *Escherichia coli* RNAP holoenzyme in the absence of Sal and *Escherichia coli* RNAP holoenzyme in the presence of Sal at a resolution sufficient to define the orientation of Sal relative to the Sal target and to define interatomic contacts between Sal and the Sal target (resolution, =3.9 Å; FIGS. 2-3).

Figure 4:
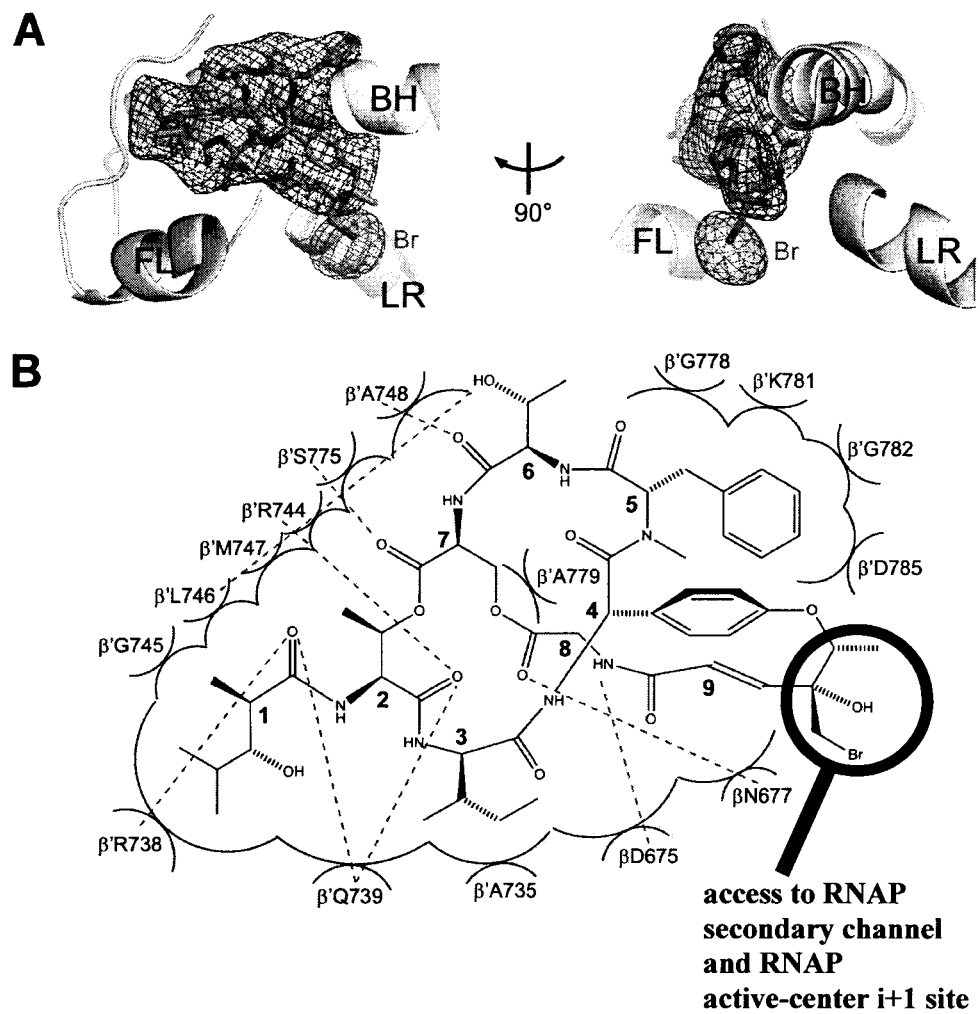
FIG. 4. Crystal structure of RNAP in complex with Sal derivative. (A) Electron density, bromine anomalous difference density, and model for *Escherichia coli* RNAP holoenzyme in complex with Sal-Br (two orthogonal views). Dark mesh, $F_o$–$F_c$ omit map for SalA (NCS averaged and contoured at 3.2σ); light mesh labelled "Br", bromine anomalous difference density (contoured at 7σ); BH, bridge helix; FL, fork loop; LR, link region. (B) Schematic summary of contacts between RNAP and Sal-Br. Black circle, part of SalA that has unobstructed access to RNAP secondary channel and RNAP active-center i+1 site. Dashed lines, H-bonds. Arcs, van der Waals interactions.

Further disclosed herein are electron density and bromine anomalous difference density for *Escherichia coli* RNAP holoenzyme in complex with Sal-Br, the compound according to general structural formula (I) wherein X is bromine (FIG. 4). The location of the Sal-Br bromine anomalous difference density peak relative to the Sal target unequivocally confirms the orientation of Sal relative to the Sal target (FIG. 4)

The Sal target is located adjacent to, and partly overlaps, the RNAP polymerase active center (Ebright et al., WO/2012/129173, 2012). It is inferred that Sal most likely inhibits RNAP by inhibiting RNAP active-center function.

The Sal target does not overlap the RNAP active-center $Mg^{2+}$ ion and does not overlap RNAP residues that interact with the DNA template, the RNA product, or the nucleoside triphosphate substrate (Ebright et al., WO/2012/129173, 2012). It is inferred Sal inhibits RNAP active-center function allosterically, through effects on RNAP conformation, rather than through direct interactions with RNAP residues that mediate bond formation, product binding, and substrate binding.

The Sal target overlaps an RNAP active-center module referred to as the "bridge-helix cap," which, in turn, comprises three active-center subregions: the "bridge-helix N-terminal hinge" (BH—$H_N$), the "F-loop," and the "link region" (Ebright et al., WO/2012/129173, 2012). It has been proposed that the BH—$H_N$ undergoes hinge-opening/hinge-closing conformational changes coupled to, and essential for, the nucleotide-addition cycle in RNA synthesis, and that the F-loop and link region, coordinate these conformational changes (Weinzierl, *BMC Biol.* 8:134, 2010; Hein & Landick, *BMC Biol.* 8:141, 2010; Kireeva et al., *BMC Biophys.* 5:11-18, 2012; Nedialkov et al., *Biochim. Biophys. Acta* 1829:187-198, 2013). It is inferred that Sal may inhibit RNAP active-center function by inhibiting BH—$H_N$ hinge-opening and/or hinge-closing (Ebright et al., WO/2012/129173, 2012).

The Sal target is located close to, but does not overlap, the target of the rifamycin antibacterial agents (e.g., rifampin, rifapentine, rifabutin, and rifalazil), which are RNAP inhibitors in current clinical use in antibacterial therapy (Ebright et al., WO/2012/129173, 2012; see Darst. *Trends Biochem. Sci.* 29:159-162, 2004; Chopra, *Curr. Opin. Investig. Drugs* 8:600-607, 2007; Villain-Guillot et al., *Drug Discov. Today* 12:200-208, 2007; Ho et al., *Curr. Opin. Struct. Biol.* 19:715-723, 2009). Consistent with the lack of overlap between the Sal target and the rifamycin target, Sal-resistant mutants are not cross-resistant to rifamycins, and rifamycin-resistant mutants are not cross-resistant to Sal (Ebright et al., WO/2012/129173, 2012).

The Sal target also is located close to, but does not overlap, the target of CBR703, an RNAP inhibitor under investigation for clinical use in antibacterial therapy (Ebright et al., WO/2012/129173, 2012; see Darst. *Trends Biochem. Sci.* 29:159-162, 2004; Chopra, *Curr. Opin. Investig. Drugs* 8:600-607, 2007; Villain-Guillot et al., *Drug Discov. Today* 12:200-208, 2007). Consistent with the lack of overlap between the Sal target and the CBR703 target, Sal-resistant mutants are not cross-resistant to CBR703, and CBR703-resistant mutants are not cross-resistant to Sal (Ebright et al., WO/2012/129173, 2012).

It is disclosed herein that the Sal target does not overlap the targets of the RNAP inhibitors streptolydigin, myxopyronin, and lipiarmycin (see Chopra, *Curr. Opin. Investig. Drugs* 8:600-607, 2007; Villain-Guillot et al., *Drug Discov. Today* 12:200-208, 2007; Ho et al., *Curr. Opin. Struct. Biol.* 19:715-723, 2009; Srivastava et al., *Curr. Opin. Microbiol.* 14:532-543, 2011). The Sal target is located adjacent to, but does not overlap, the streptolydigin target. The Sal target is distant from the myxopyronin and lipiarmycin targets. It further is disclosed herein that, consistent with the absence of overlap between the Sal target and the streptolydigin, myxopyronin, and lipiarmycin targets, Sal-resistant mutants do not exhibit cross-resistance with streptolydigin, myxopyronin, and lipiarmycin, and, conversely, streptolydigin-resistant, myxopyronin-resistant, and lipiarmycin-resistant mutants do not exhibit cross-resistance with Sal.

Salinamides: Mechanism of Inhibition of RNAP

It is disclosed herein that Sal inhibits RNAP through a mechanism that is different from the mechanisms of rifamycins, streptolydigin, myxopyronin, and lipiarmycin.

It is disclosed herein that Sal does not inhibit formation of the RNAP-promoter open complex in transcription initiation. This result indicates that Sal inhibits RNAP through a mechanism different from the mechanisms of myxopyronin and lipiarmycin (which inhibit formation of RNAP-promoter open complex).

It is disclosed herein that Sal inhibits nucleotide addition in both transcription initiation and transcription elongation. Sal inhibits both primer-dependent transcription initiation and de novo transcription initiation. In primer-dependent transcription initiation, Sal inhibits all nucleotide-addition steps, including the first nucleotide-addition step yielding a 3-nucleotide RNA product from a 2-nucleotide RNA primer and an NTP. In de novo transcription initiation, Sal inhibits all nucleotide-addition steps, including the first nucleotide-addition step yielding a 2-nucleotide RNA product from two NTPs. These results confirm that Sal inhibits RNAP through a mechanism different from the mechanisms of myxopyronin and lipiarmycin (which do not inhibit transcription elongation) and indicate that Sal inhibits RNAP through a mechanism different from the mechanism of rifamycins (which do not inhibit the first nucleotide addition step in transcription initiation and which do not inhibit transcription elongation).

It is disclosed herein that transcription inhibition by Sal does not require the RNAP active-center subregion referred to as the trigger loop. Sal inhibits wild-type RNAP and an RNAP-derivative having a deletion of the trigger loop to equal extents and with nearly equal concentration-dependences. This result indicates that Sal inhibits RNAP through a mechanism different from the mechanisms of streptolydigin (for which transcription inhibition requires the trigger loop).

It is disclosed herein that transcription inhibition by Sal is noncompetitive with respect to NTP substrate. It is inferred that Sal does not inhibit the NTP binding sub-reaction of the nucleotide-addition cycle, but, instead, inhibits one or more of the bond-formation, pyrophosphate-release, and translocation sub-reactions of the nucleotide-addition cycle.

Salinamides: Novel Sal Analogs

The syntheses disclosed herein of Sal-Br, Sal-OH, Sal-OR, Sal-SR, and Sal-NHR show that the SalA epoxide moiety and SalB chlorohydrin moieties provide chemical reactivity that can be exploited for semi-synthesis of novel Sal analogs (Examples 3-7). The observation that certain synthesized Sal analogs retain RNAP-inhibitory activity and antibacterial activity shows that certain substitutions of the SalA epoxide moiety and SalB chlorohydrin moiety can be tolerated without loss of activity (Tables 1-2). The crystal structure of RNAP-Sal indicates that the SalA epoxide moiety and SalB chlorohydrin moiety make few or no interactions with RNAP and are located at the entrance to the Sal binding pocket, directed towards the RNAP secondary channel and the RNAP active-center i+1 site (FIGS. 3-4).

These findings set the stage for structure-based design of semi-synthetic, novel Sal analogs with increased potency.

By way of example, appending a sidechain that carries hydrogen-bonding functionality at the SalA epoxide moiety or SalB chlorohydrin moiety, could provide favorable hydrogen-bonded interactions with polar residues on the floor of the RNAP secondary channel (e.g., residues β678, β1105, β1106, β'731, and β'736 in RNAP from *Escherichia coli*, and residues corresponding to, and alignable with, these residues in RNAP from other bacterial species).

By further way of example, appending a sidechain carrying negatively charged functionality at the SalA epoxide moiety or SalB chlorohydrin moiety could provide favorable electrostatic interactions with positively charged residues on the floor of the RNAP secondary channel (e.g., residues 13678, 131106, and (3'731 in RNAP from *Escherichia coli*, and residues corresponding to, and alignable with, these residues in RNAP from other bacterial species).

Administration of Pharmaceutical Compositions

The compounds described herein may be formulated as pharmaceutical compositions and administered to a mammalian host, such as a human male or female patient in a variety of forms adapted to the chosen route of administration (e.g., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound may be conveniently formulated in unit dosage form; foil example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g.; into a number of discrete loosely spaced administrations; such as multiple inhalations from an insufflator or by application of a plurality of drops into the eye.

The invention will now be illustrated by the following non-limiting Examples.

EXAMPLES

Example 1

Crystal Structure of RNAP in Complex with Sal

Crystal structures of *Escherichia coli* RNAP holoenzyme at 3.9 Å resolution and *Escherichia coli* RNAP holoenzyme in complex with SalA at 3.9 Å resolution were determined as follows:

Crystallization trials were performed using Crystal Former microfluidic chips (Microlytic, Inc.) and SmartScreen solutions (Microlytic, Inc.) (precipitant inlet: 1.5 µl screening solution; sample inlet: 1.5 µl 10 mg/ml *Escherichia coli* RNAP holoenzyme in 10 mM Tris-HCl, pH 7.9, 100 mM NaCl, 1% glycerol; 22° C.). Under one condition, small crystals appeared within two days. Conditions were optimized using the hanging-drop vapor-diffusion technique at 22° C. The optimized conditions (reservoir: 500 µl 0.1 M HEPES, pH 7.0, 0.2 M CaCl$_2$, and 18% PEG400; drop: 1 µl 10 mg/ml *Escherichia coli* RNAP holoenzyme in 10 mM Tris-HCl, pH 7.9, 100 mM NaCl, 1% glycerol plus 1 µl reservoir solution; 22° C.) yielded large crystals with dimensions of 0.2 mm×0.2 mm×0.2 mm in one week. SalA was soaked into RNAP crystals, yielding RNAP-Sal crystals, by addition of 0.2 µl 20 mM SalA or Sal-Br in (±)-2-methyl-2,4-pentanediol (Hampton Research, Inc.) to the crystallization drop and incubation 30 min at 22° C. RNAP and RNAP-SalA crystals were transferred to reservoir solutions containing 15% (v/v) (2R,3R)-(−)-2,3-butanediol (Aldrich, Inc.) and then flash-cooled with liquid nitrogen.

Diffraction data were collected from cryo-cooled crystals at Cornell High Energy Synchrotron Source beamline F1 and at Brookhaven National Laboratory beamline X25. Data were processed using HKL2000.

The structure of *Escherichia coli* RNAP holoenzyme was solved by molecular replacement using AutoMR. The search model was generated by starting with the crystal structure of *Thermus thermophilus* RNAP-promoter open complex (PDB 4G7H), deleting DNA and non-conserved protein domains, modelling *Escherichia coli* RNAP holoenzyme $\alpha^I$ and $\alpha^{II}$ subunit N-terminal domains by superimposing the crystal structure of *Escherichia coli* RNAP holoenzyme α N-terminal domain dimer (PRB 1BDF), and modelling *Escherichia coli* RNAP holoenzyme β, β', ω, and $\sigma^{70}$ subunits using Sculptor (backbone and sidechain atoms for identical residues; backbone and Cβ atoms for non-identical residues). Two RNAP molecules were present in the asymmetric unit. Crystal structures of *Escherichia coli* RNAP holoenzyme α subunit C-terminal domain (PDB 3K4G), the *Escherichia coli* RNAP holoenzyme β subunit β2-βi4 and βflap-βi9 domains (PDB 3LTI and PDB 3LUO), and *Escherichia coli* RNAP holoenzyme $\sigma^{70}$ region 2 (PDB 1 SIG) were fitted manually to the (Fo−Fc) difference electron density map. Early-stage refinement of the structure was performed using Phenix and included rigid-body refinement of each RNAP molecule in the asymmetric unit, followed by rigid-body refinement of each subunit of each RNAP molecule, followed by rigid-body refinement of 216 segments of each RNAP molecule, followed by group B-factor refinement with one B-factor group per residue, using Phenix. Density modification, including non-crystallographic-symmetry averaging and solvent flattening, were performed to remove model bias and to improve phases. The resulting maps allowed segments that were not present in, the search model to be built manually using Coot. Cycles of iterative model building with Coot and refinement with Phenix improved the model. The final *E. coli* RNAP holoenzyme model, refined to Rwork and Rfree of 0.276 and 0.325, respectively, was deposited in the PDB with accession code 4MEY.

The structure of *Escherichia coli* RNAP holoenzyme coli in complex with SalA was solved by molecular replacement in AutoMR, using the above crystal structure of *Escherichia coli* RNAP holoenzyme as the search model. After rigid-body refinement with 216 domains, an electron density feature corresponding to one molecule of SalA per holoenzyme was clearly visible in the (Fo−Fc) difference map. A structural model of SalA derived from the crystal structure of SalB (CSD 50962; enantiomorph corrected based on Moore et al., et al., *J. Org. Chem.*, 64:1145-1150, 1999) was fitted to the (Fo−Fc) difference map with minor adjustments of SalA conformation. The final *Escherichia coli* RNAP holoenzyme-SalA complex model, refined to Rwork and Rfree of 0.286 and 0.325, respectively, was deposited in the PDB with accession code 4MEX.

The structure of *E. coli* RNAP holoenzyme in complex with Sal at 3.9 Å resolution shows unambiguous experimental electron density for Sal in the genetically-defined Sal target, confirming the hypothesis that the Sal target represents the Sal binding site on RNAP (FIG. 2).

The structure shows that Sal binds within the RNAP bridge-helix cap, making direct interactions with the BH—$H_N$, the fork loop, and the link region (FIGS. 2-3).

Sal makes direct interactions with all residues at which substitutions conferring highest-level (≥128-fold) Sal-resistance are obtained (β' residues R738, A779, and G782, and β residues D675 and N677; FIG. 3).

Six residues that make direct contact with SalA are conserved across Gram-positive bacterial RNAP, Gram-negative bacterial RNAP, and human RNAP. Eight residues that contact Sal are conserved in Gram-positive bacterial RNAP and Gram-negative bacterial RNAP, but are not conserved, and indeed are radically different, in human RNAP. The observed interactions account for and explain the observation that Sal inhibits Gram-positive and Gram-negative bacterial RNAP, but does not inhibit human RNAP.

Sal binds within a ~600 Å$^3$ pocket formed by the BH—$H_N$, the fork loop, and the link region. Backbone atoms of residues that form the pocket have the same conformations in RNAP holoenzyme in the absence of Sal and in RNAP holoenzyme in complex with Sal, indicating that the pocket pre-exists in RNAP holoenzyme in the absence of Sal.

The pocket opens at one end onto the RNAP secondary channel and the RNAP active-center "i+1" NTP-insertion site. It seems likely that Sal enters the pocket from the RNAP secondary channel or the active-center "i+1" site.

Within the binding pocket, Sal residues 4, 5, 7, and 8 interact with the RNAP BH—$H_N$, Sal residues 1-3 and 6-7 interact with the RNAP fork loop, and Sal residues 8 and 9 interact with the RNAP link region (FIG. 3). Sal residue 9 is at the end of the pocket that opens onto the RNAP secondary channel and the active-center "i+1" site (FIG. 3). The Sal residue-9 epoxide moiety and methyl moiety extend into this opening and make only limited interactions with residues of RNAP (FIG. 3).

The crystal structure of the RNAP-Sal complex also defines effects of Sal on RNAP conformation.

The crystal structure of RNAP-Sal shows that Sal interacts with the BH—$H_N$ in an "open" (unbent) state. This conformation is different from the "closed" (bent) BH—$H_N$ conformation that has been observed in molecular-dynamics simulations of nucleotide-addition reactions in transcription elongation complexes, and that has been postulated to serve as an intermediate in the pyrophosphate-release and/or translocation reactions of the nucleotide-addition cycle (Weinzierl, BMC Biol. 8:134, 2010; Hein & Landick, BMC Biol. 8:141, 2010; Kireeva et al., *BMC Biophys.* 5:11-18, 2012; Nedialkov et al., *Biochim. Biophys. Acta* 1829:187-198, 2013). It is inferred that Sal interacts with an "open" (unbent) BH—$H_N$ conformational state, and it is hypothesized that, through its interactions with that state, Sal stabilizes that state and inhibits BH—$H_N$ conformational dynamics required for nucleotide addition.

In the crystal structure of RNAP-Sal, the RNAP active-center trigger loop is disordered. Modeling indicates that the structure of RNAP-Sal could accommodate the "open" (unfolded) trigger loop conformations observed in crystal structures of some transcription initiation and elongation complexes, but could not accommodate the "closed" (folded) trigger loop conformations observed in other crystal structure of transcription initiation and elongation complexes. It is inferred that Sal favors "open" (unfolded) trigger loop conformational states, and may disfavor the "closed" (folded) trigger loop conformational states. However, experiments with an RNAP derivative lacking the trigger loop indicate that the trigger loop is not essential for transcription inhibition by Sal. Therefore, although effects of Sal on trigger loop conformation could contribute to transcription inhibition by Sal, they are neither necessary nor sufficient for transcription inhibition by Sal.

The interactions observed in the structure, or predicted based on the structure, suggest opportunities for preparation of novel Sal analogs with improved potencies by use of semisynthesis or by total synthesis.

The structure shows that the SalA residue-9 epoxide moiety is directed toward the RNAP secondary channel and RNAP active-center "i+1" site (FIG. 3) but makes limited interactions with RNAP (FIG. 3). The SalA epoxide can be altered with little or no loss of activity (Tables 1-2), and has unique chemical reactivity (Examples 3-5). Accordingly, it is inferred herein that it should be possible—by semi-synthesis or by total synthesis—to append at the SalA residue 9 epoxide moiety by chemical functionality that makes favorable interactions with the RNAP secondary channel or active-center "i+1" site, thereby increasing the potency of RNAP inhibitory activity and potentially increasing the potency of antibacterial activity.

The structure predicts that the SalB residue-9 chlorohydrin moiety likewise makes limited interactions with RNAP and is directed toward the RNAP secondary channel and RNAP active-center "i+1" site and. The SalB chlorohydrin can be altered with little loss of activity (Tables 1-2), and has unique chemical reactivity (Examples 6-7). Accordingly, it is inferred herein that it should be possible—by semi-synthesis or by total synthesis—to append at the SalB residue-9 chlorohydrin moiety chemical functionality that makes favorable interactions with the RNAP secondary channel or active-center "i+1" site, thereby increasing the potency of RNAP inhibitory activity and potentially increasing the potency of antibacterial activity.

By way of example, appending a sidechain that carries hydrogen-bonding functionality at the SalA residue-9 epoxide moiety or SalB residue-9 chlorohydrin moiety, could allow for favorable hydrogen-bonded interactions with polar residues on the floor of the RNAP secondary channel (e.g., residues β678, β1105, β1106, β'731, and β'736 in RNAP from *Escherichia coli*, and residues corresponding to, and alignable with, these residues in RNAP from other bacterial species).

By further way of example, appending a sidechain carrying negatively charged functionality at the SalA residue-9 epoxide moiety or SalB residue-9 chlorohydrin moiety could allow for favorable electrostatic interactions with positively charged residues on the floor of the RNAP secondary channel (e.g., residues β678, β1106, and β'731 in RNAP from *Escherichia coli*, and residues corresponding to, and alignable with, these residues in RNAP from other bacterial species).

Example 2

Crystal Structure of RNAP in Complex with Sal Derivative

To confirm the binding position and binding orientation of Sal inferred from the crystal structure of RNAP-SalA, x-ray diffraction data and bromine anomalous scattering data were collected for crystals of *Escherichia coli* RNAP holoenzyme soaked with the bromine-containing Sal derivative Sal-Br (compound 3; crystal soaks, structure determination, and structure refinement performed essentially as described for SalA in Example 1). Sal-Br contained a residue-9 bromohydrin moiety analogous to the residue-9 chlorohydrin moiety of SalB, and was prepared by semi-synthesis from SalA, exploiting the chemical reactivity of the SalA residue-9 epoxide (Example 3). Sal-Br exhibited essentially full RNAP-inhibitory activity and antibacterial activity (Tables 1-2).

Electron density for Sal-Br from crystals of RNAP-Sal-Br complex matched electron density for SalA in the RNAP-SalA complex. Bromine anomalous difference density showed a single peak (FIG. 3). The peak was located adjacent to the electron density for Sal-Br, in the position predicted for the bromine atom of the Sal-Br residue-9 bromohydrin carbon atom (FIG. 3). The results unequivocally define the SalA and Sal-Br binding positions and binding orientations.

Example 3

Synthesis of Sal Derivatives Exploiting Reactivity of SalA Epoxide: Sal-Br (Compound 3)

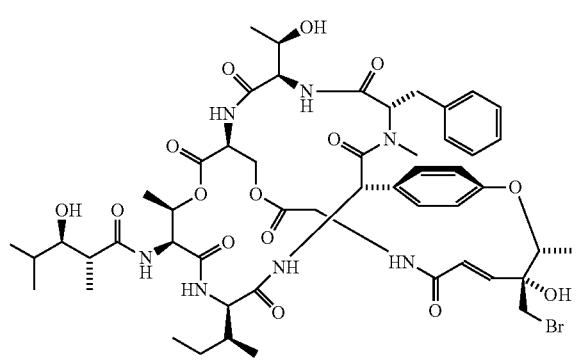

SalA (1; 5 mg; 4.9 µmol; prepared as in Trischman et al., *J. Am. Chem. Soc.*, 116:757, 1994; provided by William Fenical, Scripps Institution of Oceanography) was dissolved in 0.25 ml chloroform at 25° C. To the solution was added 48% HBr (10 µl, 89 µmol; Aldrich). The reaction mixture was stirred 15 min at 25° C., and then quenched with 200 µl 50% sodium bicarbonate. The organic layer was separated, re-washed with 100 µl water, and dried to a white solid. Products were purified using silica flash chromatography (0-10% methanol in chloroform as eluent). Yield: 5 mg, 93%. MS (MALDI): calculated: m/z 1099.41, 1101.41. Found: 1122.48, 1124.48 (M+Na$^+$).

Example 4

Synthesis of Sal Derivatives Exploiting Reactivity of SalA Epoxide: Sal-OH (Compound 4)

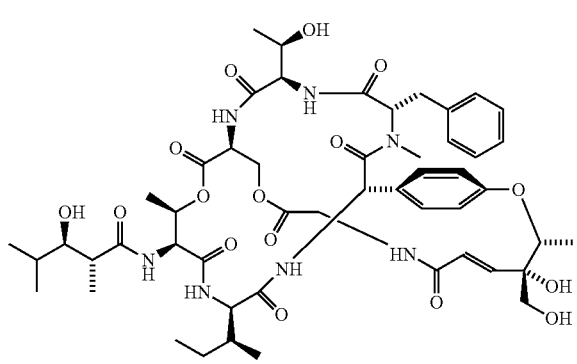

SalA (1; 1 mg; 0.98 µmol; prepared as in Trischman et al., *J. Am. Chem. Soc.*, 116:757, 1994; provided by William Fenical, Scripps Institution of Oceanography) was dissolved in 0.5 ml n-butanol, and 1 μl 98% sulfuric acid was added. The reaction mixture was heated 10 min at 100° C. in a microwave reactor (Initiator, Biotage, Inc.), cooled to 25° C., and then neutralized with 400 μl 50% sodium bicarbonate. The organic layer was retrieved and evaporated to dryness. Products were purified by reversed-phase HPLC [Luna C18, 5μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 4 eluted at 38 min. Yield: 80 μg, 7.7%. MS (MALDI): calculated: m/z 1037.50. Found: 1060.50 (M+Na$^+$).

Example 5

Synthesis of Sal Derivatives Exploiting Reactivity of SalA epoxide: Sal-OR 5.1. Sal-OBu A (compound 5A) and Sal-OBu B (compound 5B)

SalA (1; 1 mg; 0.98 μmol; prepared as in Trischman et al., *J. Am. Chem. Soc.*, 116:757, 1994; provided by William Fenical, Scripps Institution of Oceanography) was dissolved in 0.5 ml n-butanol, and 1 μl 98% sulfuric acid was added. The reaction mixture was heated 10 min at 100° C. in a microwave reactor (Initiator, Biotage, Inc.), cooled to 25° C., and then neutralized with 400 μl 50% sodium bicarbonate. The organic layer was retrieved and evaporated to dryness. Products were purified by reversed-phase HPLC [Luna C18, 5μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 5A eluted at 56 min. Compound 5B eluted at 53 min.

Compound 5A: Yield: 140 μg, 9%. MS (MALDI): calculated: m/z 1093.62. Found: 1094.63, 1116.59 (M+Na$^+$).

Compound 5B: Yield: 69 μg, 4.4%. MS (MALDI): calculated: m/z 1093.62. Found: 1094.63, 1116.59 (M+Na$^+$).

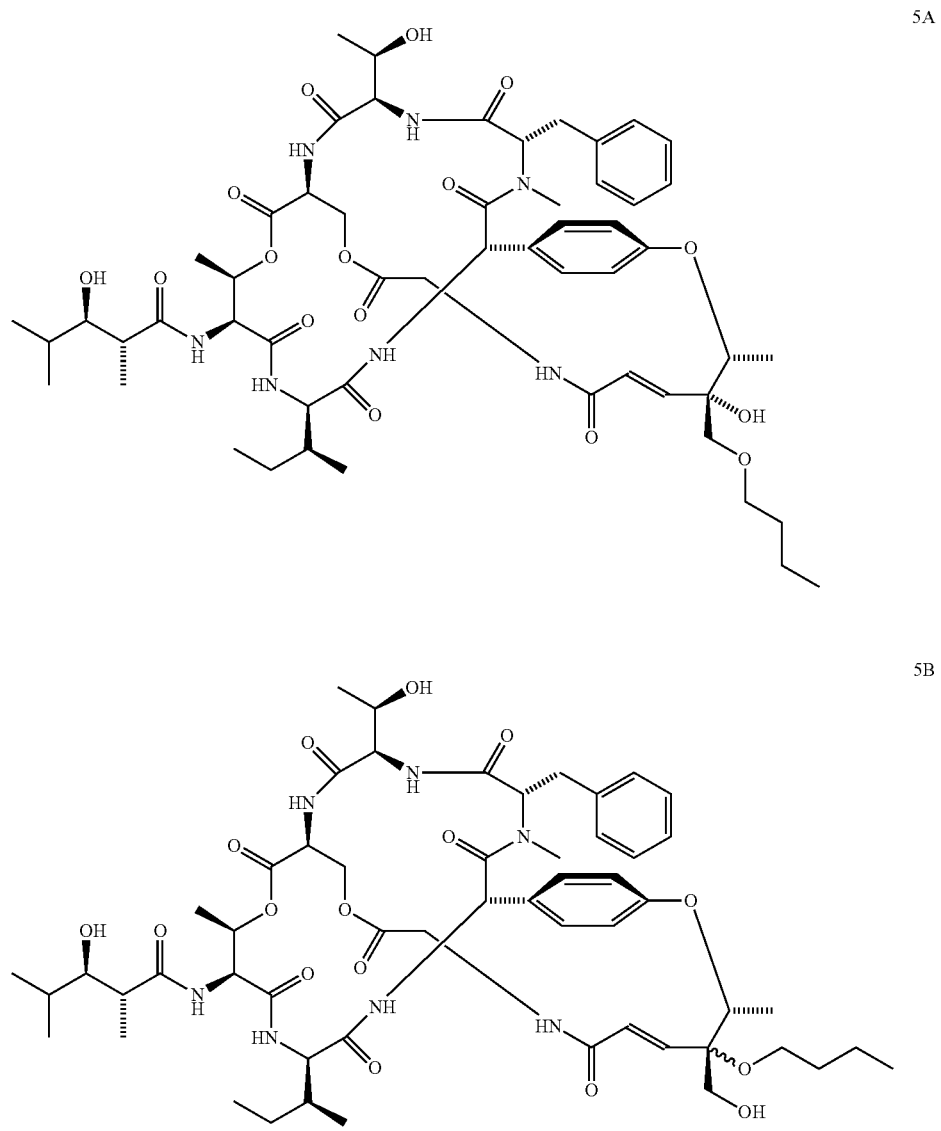

Example 6

Synthesis of Sal Derivatives Exploiting Reactivity of SalA Epoxide: Sal-SR 6.1. Sal-SBu (compound 6)

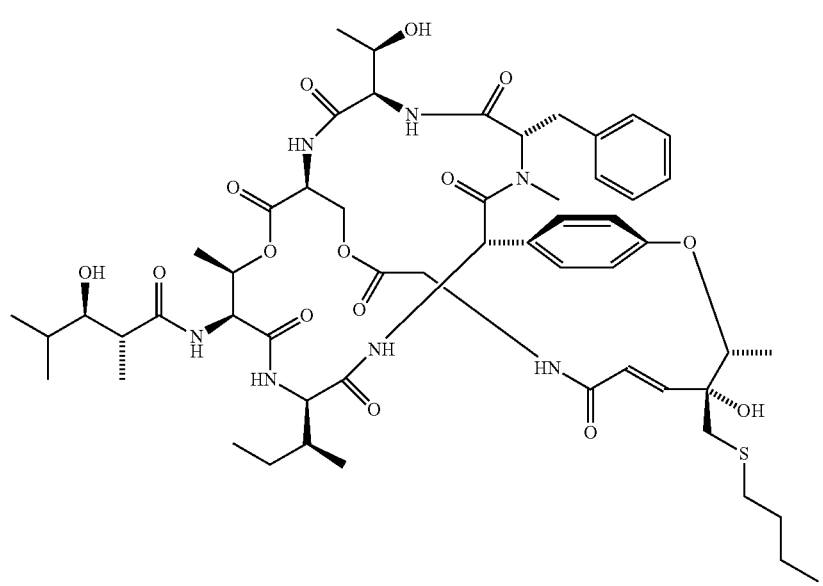

6

Compound 6 is prepared as described for compound 5A, except that 0.5 ml benzene, 5 μmol lithium perchlorate, and 10 μmol butanethiol are used in place of 0.5 ml n-butanol, and 1 μl 98% sulfuric acid.

Example 7

Synthesis of Sal Derivatives Exploiting Reactivity of SalB Chlorohydrin: Sal-NHR 7.1. Sal-NH(CH$_2$)$_3$NHBoc (compound 7)

SalB (2; 5 mg; 4.7 μmol; prepared as in Trischman et al., *J. Am. Chem. Soc.*, 116:757, 1994; provided by William Fenical, Scripps Institution of Oceanography) was dissolved in 1 ml ethanol, and N-Boc-1,3-diaminopropane (3.4 mg, 19.5 μmol; Aldrich, Inc.) was added. The reaction mixture was heated 5 min at 150° C. in a microwave reactor (Initiator; Biotage, Inc.), cooled to 25° C., and then evaporated to dryness. Products were purified by reversed-phase HPLC [Luna C18, 5μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 7 eluted at 35 min. Yield: 0.261 mg, 4.5%. MS (MALDI): calculated: m/z 1193.39. Found: 1216.71 (M+Na$^+$).

7

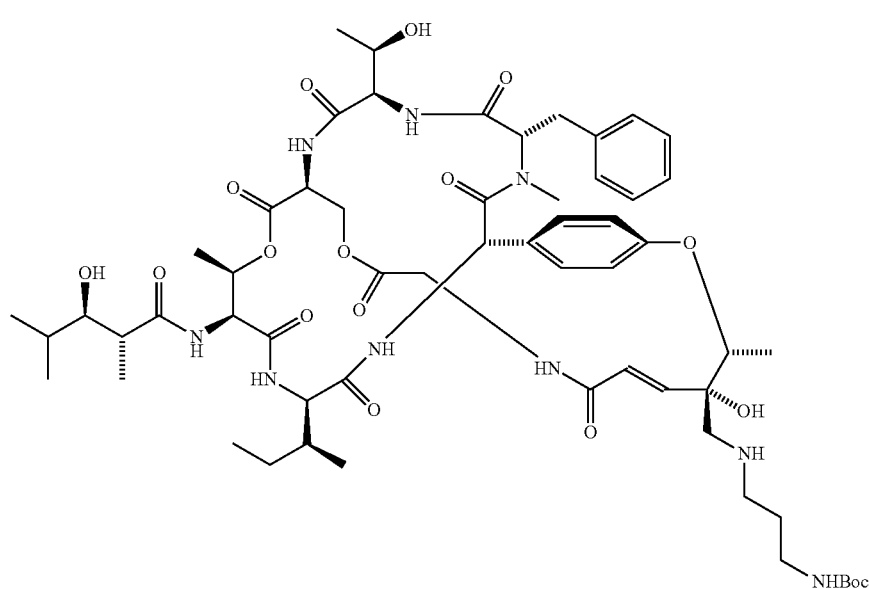

7.2. Sal-NH(CH$_2$)$_3$NHBoc (Compound 8)

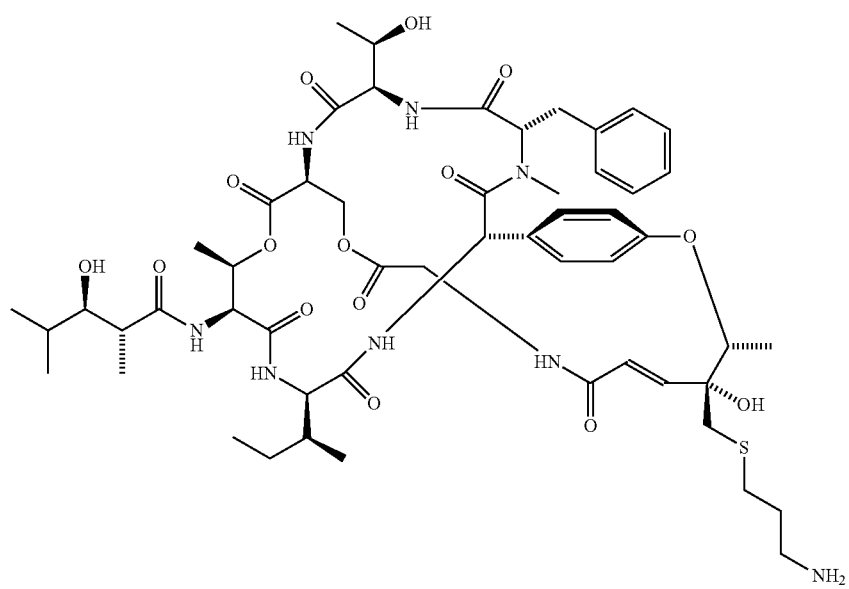

8

Compound 8 is prepared from compound 7 by reaction with 50 µl trifluoroacetic acid in 200 µl chloroform for 30 min at 25° C., and is purified by reversed-phase HPLC.

7.3. Sal-NH(CH$_2$)$_6$NHBoc (Compound 9)

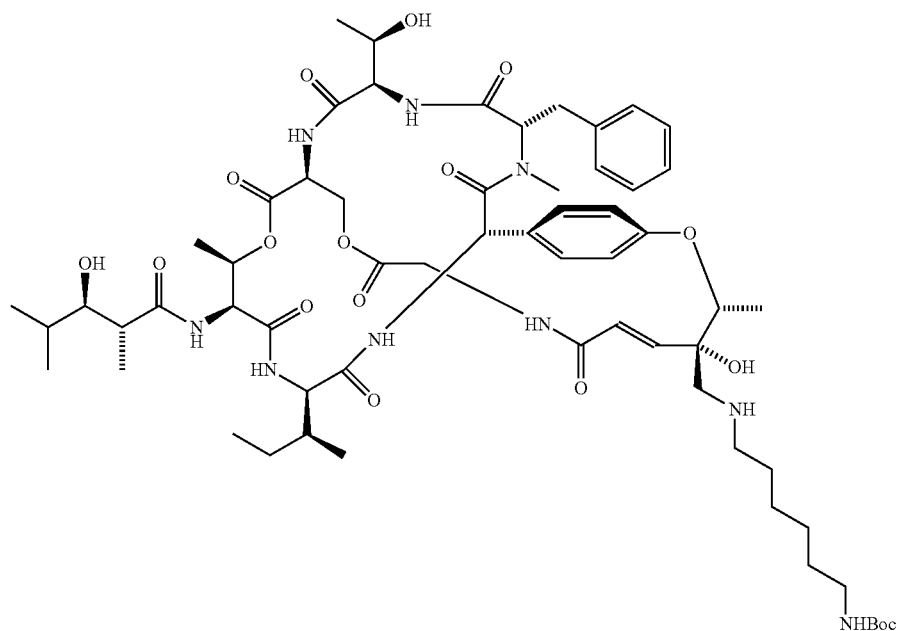

9

SalB (2; 10 mg; 9.5 µmol; prepared as in Trischman et al., *J. Am. Chem. Soc.*, 116:757, 1994; provided by William Fenical, Scripps Institution of Oceanography) was dissolved in 1 ml ethanol, and N-Boc-1,6-diaminohexane (4.1 mg, 18.95 µmol; Acros, Inc.) was added. The reaction mixture was heated 6 min at 160° C. in a microwave reactor (Initiator; Biotage, Inc.), cooled to 25° C., and then evaporated to dryness. Products were purified by reversed-phase HPLC [Luna C18, 5µ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 8 eluted at 39 min. Yield: 1.46 mg, 14%. MS (MALDI): calculated: m/z 1235.67. Found: 1236.56 (M+H$^+$), 1258.58 (M+Na$^+$).

7.4. Sal-NH(CH$_2$)$_6$NHBoc (compound 10)

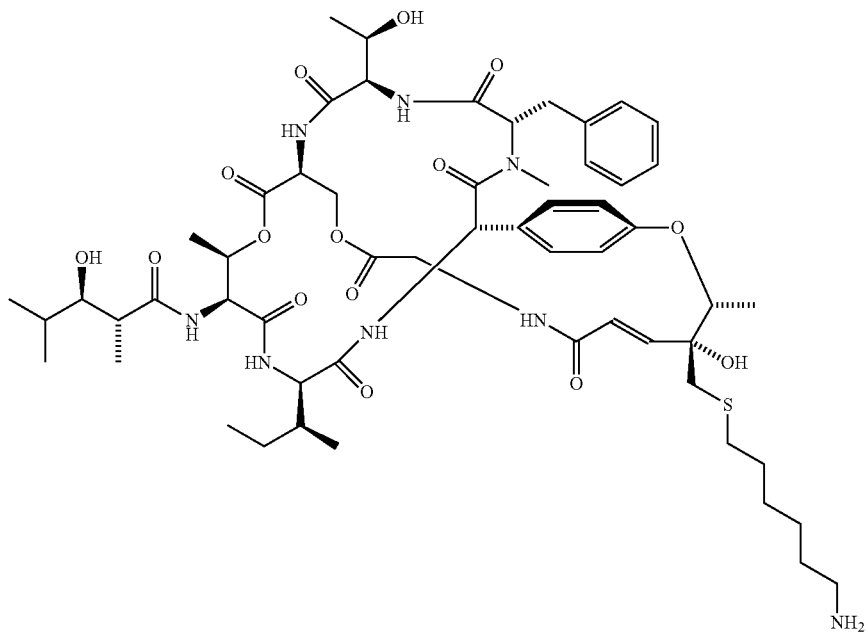

10

Compound 10 is prepared from compound 9 by reaction with 50 µl trifluoroacetic acid in 200 µl chloroform for 30 min at 25° C. and is purified by reversed-phase HPLC.

Example 8

RNAP-Inhibitory Activity

Radiochemical RNAP assays with *Escherichia coli* RNAP and *Staphylococcus aureus* RNAP were performed as follows: Reaction mixtures contained (10 µl): 0-100 µM test compound, bacterial RNAP holoenzyme [75 nM *Escherichia coli* RNAP holoenzyme (prepared as in Mukhopadhyay et al., *Meths. Enzymol.* 371:144-159, 2003) or 75 nM *Staphylococcus aureus* RNAP core enzyme and 300 nM *Staphylococcus aureus* σ$^4$ (prepared as in Srivastava et al., *Curr. Opin. Microbiol.* 14:532-543, 2011)], 20 nM DNA fragment N25-lacUV5-14 [positions −100 to −1 of the bacteriophage T5 N25 promoter followed by positions +1 to +29 of the lacUV5 (+10A; +15C) promoter; prepared by PCR amplification of a synthetic nontemplate-strand oligodeoxyribonucleotide], 0.5 mM ApA, 100 µM [α$^{32}$P]UTP (0.2 Bq/fmol), 100 µM ATP, and 100 µM GTP in TB (50 mM Tris-HCl, pH 7.9, 100 mM KCl, 10 mM MgCl$_2$, 1 mM DTT, 100 µg/ml bovine serum albumin, and 5% glycerol). Reaction components except DNA, ApA, and NTPs were pre-incubated 10 min at 24° C.; DNA was added and reaction mixtures were incubated 10 min at 37° C.; ApA, 0.15 µl 7 µM [α$^{32}$P]UTP (200 Bq/fmol), ATP, and GTP were added and reaction mixtures were incubated 5 min at 37° C.; and 0.5 µl 2 mM UTP was added and reaction mixtures were incubated 5 min at 37° C. Reactions were terminated by adding 10 µl loading buffer (80% formamide, 10 mM EDTA, 0.02% bromophenol blue, and 0.02% xylene cyanol) and heating 2 min at 95° C. Products were applied to 7 M urea 15% polyacrylamide (19:1 acrylamide:bisacrylamide) slab gels (Bio-Rad), electrophoresed in TBE (90 mM Tris-borate, pH 8.0, and 2 mM EDTA), and analyzed by storage-phosphor scanning (Typhoon; GE Healthcare, Inc.).

Radiochemical assays with human RNAP I, II, and III were performed essentially as described [Sawadogo and Roeder, *Cell* 43:165-75, 1985]. Reaction mixtures contained (20 µl): 0-100 µM test compound, 8 U HeLaScribe Nuclear Extract (Promega, Inc.), 1 µg human placental DNA (Sigma-Aldrich), 400 µM ATP, 400 µM [α$^{32}$P]UTP (0.11 Bq/fmol), 400 µM CTP, 400 µM GTP, 50 mM Tris-HCl, pH 8.0, 7 mM HEPES-NaOH, 70 mM (NH$_4$)$_2$SO$_4$, 50 mM KCl, 12 mM MgCl$_2$, 5 mM DTT, 0.1 mM EDTA, 0.08 mM phenylmethylsulfonyl fluoride, and 16% glycerol. Reaction components other than DNA and NTPs were pre-incubated 10 min at 30° C., DNA was added and reaction mixtures were incubated 15 min at 30° C., NTPs were added and reaction mixtures were incubated 60 min at 30° C. Reaction mixtures were spotted on DE81 filter discs (Whatman, Inc.; pre-wetted with water) and incubated 1 min at room temperature. Filters were washed with 3×3 ml Na$_2$HPO$_4$, 2×3 ml water, and 3 ml ethanol, using a filter manifold (Hoefer, Inc.). Filters were placed in scintillation vials containing 10 ml Scintiverse BD Cocktail (Thermo Fisher, Inc.), and radioactivity was quantified by scintillation counting (LS6500; Beckman-Coulter, Inc.).

Fluorescence-detected RNAP assays with *Escherichia coli* RNAP were performed by a modification of the procedure of Kuhlman et al., *Anal. Biochem.* 324:183-190, 2004]. Reaction mixtures contained (20 µl): 0-100 nM test compound, 75 nM *Escherichia coli* RNAP σ$^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM MgCl$_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM CaCl$_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)].

Half-maximal inhibitory concentrations (IC50s) were calculated by non-linear regression in SigmaPlot (SPSS, Inc.).

Example 9

Antibacterial Activity

Antibacterial activity was quantified using broth microdilution [Clinical and Laboratory Standards Institute (CLSI/NCCLS), *Methods for Dilution Antimicrobial Susceptibility Tests for Bacteria That Grow Aerobically; Approved Standard, Eighth Edition. CLIS Document M07-A8* (CLIS, Wayne Pa.), 2009]. Assays with *Enterobacter cloacae* ATCC 13047, *Pseudomonas aeruginosa* ATCC10145, and *Escherichia coli* D21f2tolC, employed a starting cell density of 2-5×10$^5$ cfu/ml, Mueller Hinton II cation adjusted broth (BD Biosciences, Inc.), and an air atmosphere. Assays with *Haemophilus influenzae* ATCC49247 and *Neisseria gonorrhoeae* ATCC 19424 employed a starting cell density of 2-5×10$^5$ cfu/ml, *Haemophilus* Test Medium broth (Barry et al., 1993) and a 5% CO2/95% air atmosphere. MIC50 was defined as the minimal concentration resulting in ≥50% inhibition of bacterial growth.

Example 10

Cytotoxicity

MICs for mammalian cells (Vero E6) in culture were quantified using CellTiter96 assay (Promega. Inc.; procedures as specified by the manufacturer), Screening data for SalA and SalB (compounds 1 and 2) and representative compounds of this invention (compounds 3-9) are presented in Tables 1-2:

TABLE 1

RNAP-inhibitory activity (fluorescent-detected RNAP assays)

| compound | IC50 *Escherichia coli* RNAP (μM) | IC50 human RNAP I/II/III (μM) |
|---|---|---|
| SalA (1) | 1 | >100 |
| SalB (2) | 1 | >100 |
| Sal-Br (3) | 3 | >100 |
| Sal-OH (4) | 2 | |
| Sal-OBu A (5A) | 6 | |
| Sal-OBu B (5B) | >25 | |
| Sal-NH(CH$_2$)$_3$NHBoc (7) | 0.6 | |
| Sal-NH(CH$_2$)$_6$NHBoc (9) | 1 | |

TABLE 2

Antibacterial activity

| compound | MIC50 *Escherichia coli* D21f2toIC (μg/ml) | MIC50 *Enterobacter cloacae* ATCC 13047 (μg/ml) |
|---|---|---|
| SalA (1) | 0.024 | 1.56 |
| SalB (2) | 0.098 | 6.25 |
| Sal-Br (3) | 0.049 | 1.56 |
| Sal-OH (4) | 0.78 | 25 |
| Sal-OBu A (5A) | 1.56 | 12.5 |
| Sal-NH(CH$_2$)$_3$NHBoc (7) | 1.56 | 100 |
| Sal-NH(CH$_2$)$_6$NHBoc (9) | 0.78 | 25 |

TABLE 3

Absence of cytotoxicity to mammalian cells in culture

| compound | MIC50 Vero E6 ATCC CRL1586 (μg/ml) |
|---|---|
| SalA (1) | >100 |
| SalB (2) | >100 |
| Sal-Br (3) | >100 |

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:
1. A compound of formula (I):

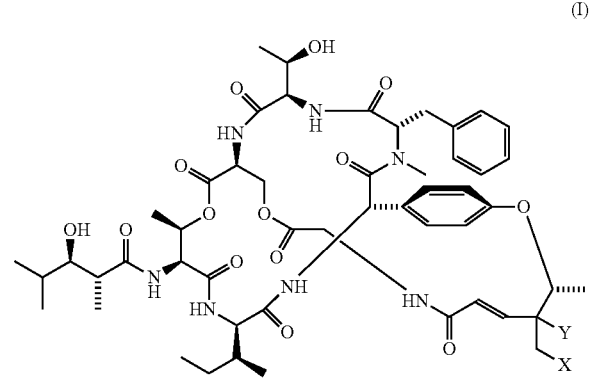

wherein:
X is one of —Br, —I, —OR, —SR, and —NHR; Y is one of —Br, —I, —OR, —SR, and —NHR; and at least one of X and Y is OH;
each R is independently H or a branched or unbranched, saturated or unsaturated, hydrocarbon chain, having from 3 to 15 carbon atoms, wherein one or more of the carbon atoms is optionally replaced by (—O—) or (—NR$^a$—), and wherein the chain is optionally substituted on carbon with one or more substituents independently selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, heteroaryloxy, a hydrogen-bonding group, and a negatively charged functional group; and each R$^a$ is independently H or ($C_1$-$C_6$)alkyl;

or a salt thereof.

2. The compound of claim h which is a compound of formula (Ia):

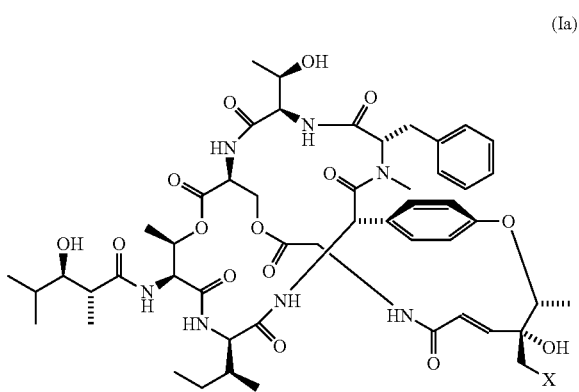

(Ia)

or a salt thereof.

3. The compound of claim 2, wherein X is one of —Br, —I, —OR, and —SR; wherein R consists of a chain of about 3 to about 6 consecutively bonded non-hydrogen atoms, and contains a hydrogen-bonding or negatively charged functional group.

4. The compound of claim 3, wherein R consists of a chain of about 3 to about 4 consecutively bonded non-hydrogen atoms, and contains a hydrogen-bonding or negatively charged functional group.

5. The compound of claim 1, wherein R is a branched or unbranched, saturated or unsaturated, hydrocarbon chain, having from 3 to 8 carbon atoms, wherein one or more of the carbon atoms is optionally replaced by (—O—) or (—NR$^a$—), and wherein the chain is optionally substituted on carbon with one or more substituents independently selected from the group consisting of ($C_1$-$C_6$)alkoxy, ($C_1$-$C_6$)alkanoyl, ($C_1$-$C_6$)alkanoyloxy, ($C_1$-$C_6$)alkoxycarbonyl, halo, hydroxy, oxo, carboxy, aryl, aryloxy, a hydrogen-bonding group, and a negatively charged functional group.

6. The compound of claim 1, wherein X is one of —Br and —I.

7. The compound of claim 1, wherein X is one of —OR, —SR, and —NHR, and R is H or consists of a chain of about 3 to about 8 consecutively bonded non-hydrogen atoms and contains a hydrogen-bonding or negatively charged functional group.

8. The compound of claim 7, wherein R consists of a chain of about 3 to about 6 consecutively bonded non-hydrogen atoms and contains a hydrogen-bonding or negatively charged functional group.

9. The compound of claim 1, wherein the hydrogen-bonding group is selected from amine, hydroxyl, thiol, ether, thioether, carbonyl, thionyl, carboxyl, thiocarboxyl, amide, thioamide, ester, thioester, sulfonic acid sulfonic acid ester, sulfonamide, phosphoric acid, phosphoric acid ester, phosphonamide, boronic acid, boronic acid ester, pyrrole, pyrrolidine, carbazole, pyrroline, indole, isoindole, indoline, indolizine, furan, pyran, benzofuran, thiophene, benzothiophene, pyridine, quinoline, isoquinoline, quinazoline, napthyridine, oxazole, isoxazole, benzoxazole, thiazole, isothiazole, benthiazole, oxadiazole, thiadiazole, imidazole, triazole, tetrazole, benzimidazole, pyrazole, pyrazine, pyridazine, pyrimidine, triazine, indazole, purine, pteridine, phthalazine, quinoxaline, quinazoline, cinnoline, acridine, phenazine, phenothiazine, phenoxazine, and ionized forms and salts thereof.

10. The compound of claim h wherein the negatively charged functional group is selected from carboxyl, thiocarboxyl, sulfonic acid, phosphoric acid, phosphoric acid ester, boronic acid, triazole, tetrazole, purine, and thiol, and ionized forms and salts thereof.

11. The compound of claim 1, wherein X is one of —O($CH_2$)$_n$C(OH)(R')R", —O($CH_2$)$_n$C(O)R', —O($CH_2$)$_n$C(O)OR', —O($CH_2$)$_n$C(O)NR'R", —O($CH_2$)$_n$OC(H)(R')R", —S($CH_2$)$_n$C(OH)(R')R", —S($CH_2$)$_n$C(O)R', —S($CH_2$)$_n$C(O)OR', —S($CH_2$)$_n$C(O)NR'R", —S($CH_2$)$_n$OC(H)(R')R", —NH($CH_2$)$_n$C(OH)(R')R", —NH($CH_2$)$_n$C(O)R', —NH($CH_2$)$_n$C(O)OR', —NH($CH_2$)$_n$C(O)NR'R", and —NH($CH_2$)$_n$OC(H)(R')R"; wherein n is 1, 2, 3, 4, 5, 6, or 7; and wherein R' and R" each independently is one of H, $C_1$-$C_3$alkyl, and $C_1$-$C_3$ alkyl substituted by one or more halogen.

12. The compound of claim 11, wherein n is 1, 2, 3, 4, or 5.

13. The compound of claim 1, which is selected from:

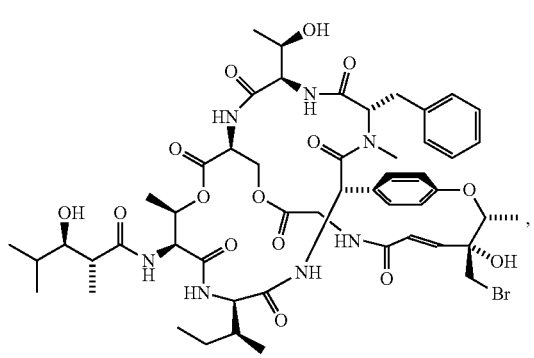

3

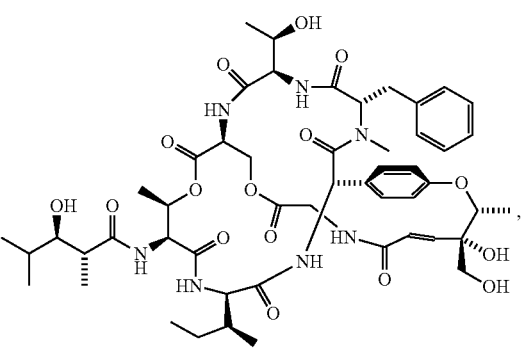

4

-continued
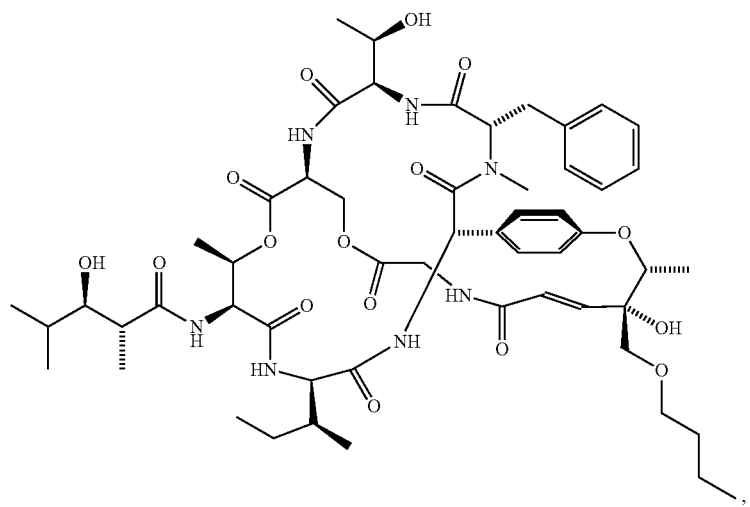
5A
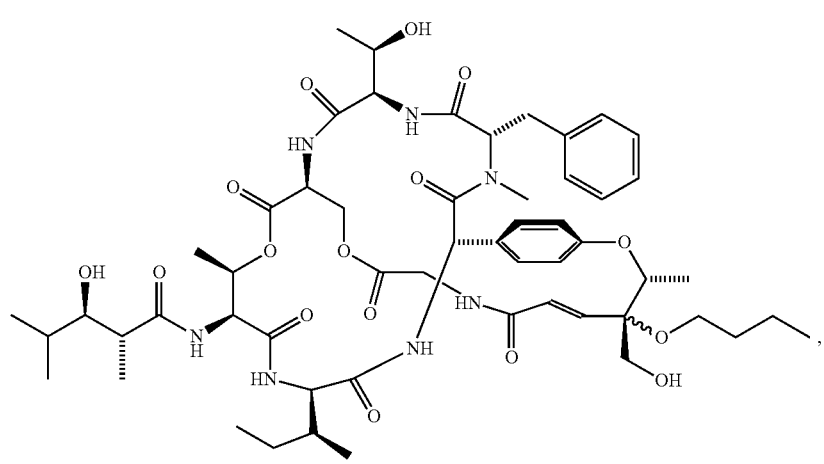
5B
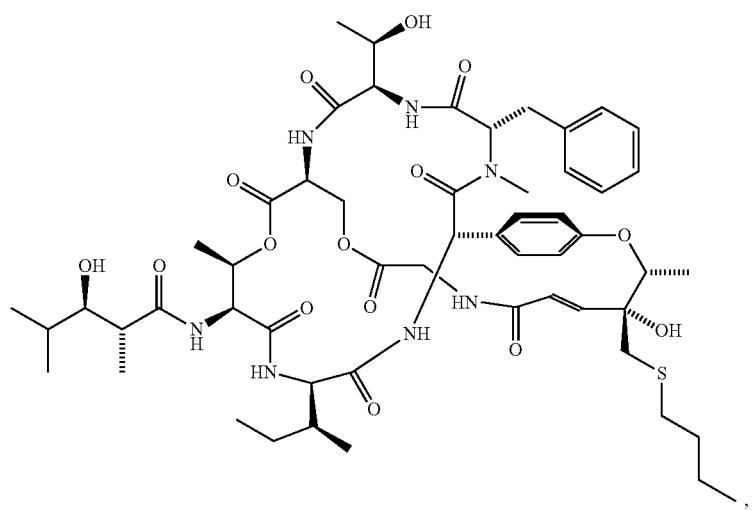
6

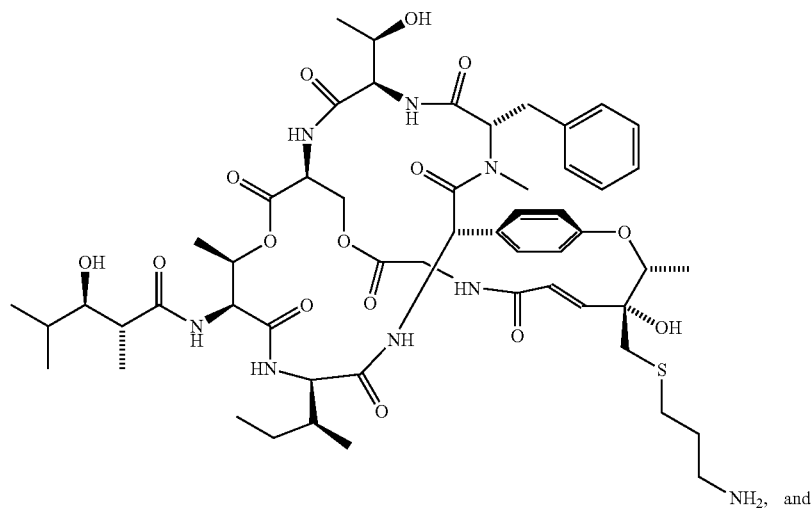
8
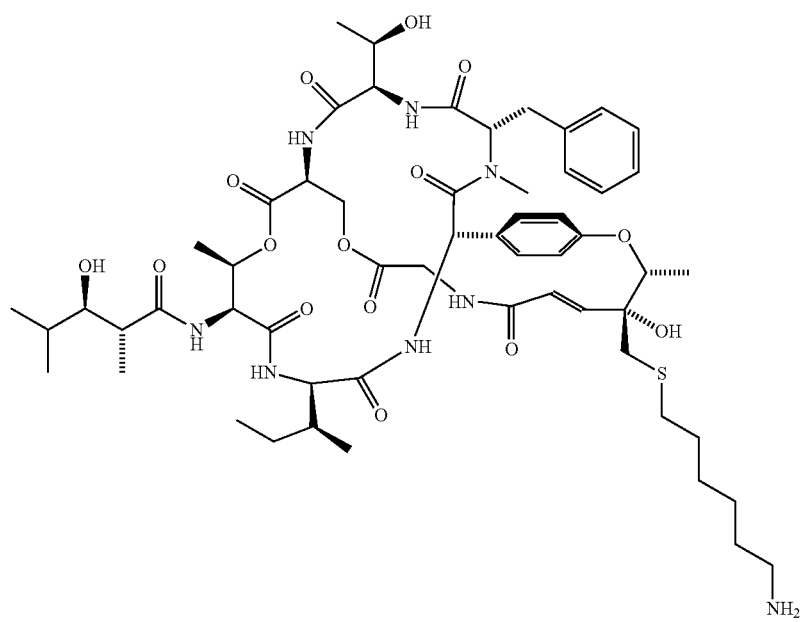
10
and salts thereof.
14. A pharmaceutical composition comprising a compound according to claim 1, or a pharmaceutically acceptable salt thereof, and a pharmaceutically acceptable carrier.

15. The compound selected from the group consisting of:
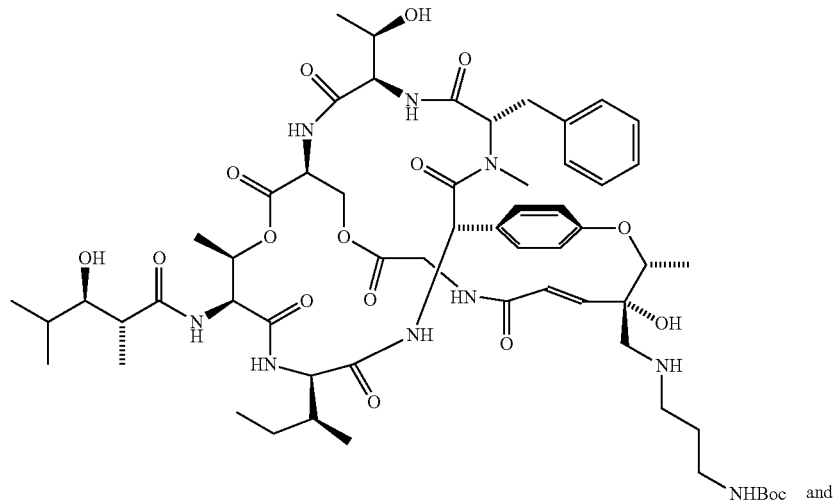
7
and
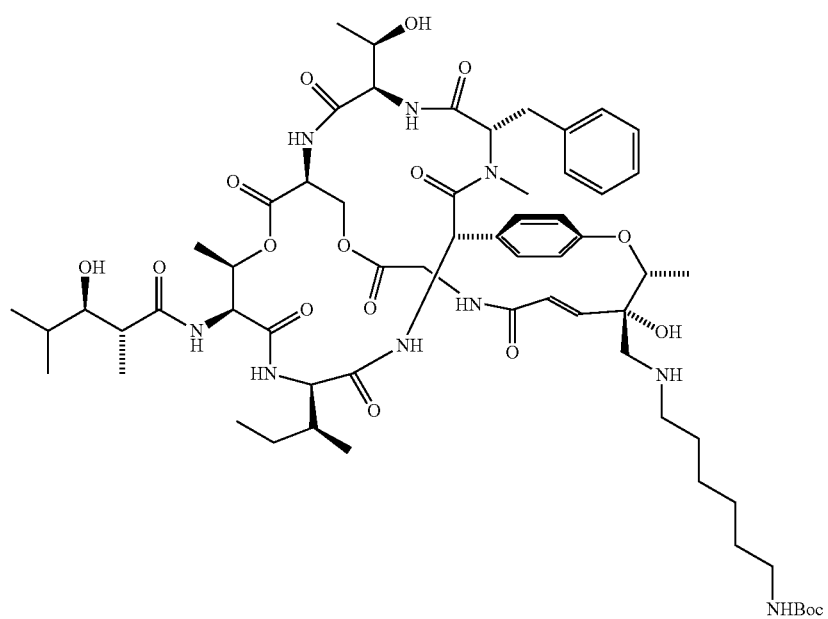
9
and salts thereof.
* * * * *